United States Patent
Sachanandani et al.

(10) Patent No.: US 10,311,533 B2
(45) Date of Patent: Jun. 4, 2019

(54) METHOD AND SYSTEM TO ENABLE PHYSICIAN LABELS ON A REMOTE SERVER AND USE LABELS TO VERIFY AND IMPROVE ALGORITHM RESULTS

(75) Inventors: Haresh G. Sachanandani, Shoreview, MN (US); Shelley Cazares, Minneapolis, MN (US); Jon Peterson, Mahtomedi, MN (US); Robert J. Sweeney, Woodbury, MN (US); Kevin J. Stalsberg, White Bear Lake, MN (US); Krzysztof Z. Siejko, Maple Grove, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2228 days.

(21) Appl. No.: 11/616,460

(22) Filed: Dec. 27, 2006

(65) Prior Publication Data

US 2008/0162183 A1   Jul. 3, 2008

(51) Int. Cl.
   *G06Q 50/22*   (2018.01)
   *G06Q 10/10*   (2012.01)
   *G16H 50/20*   (2018.01)
   *G06F 19/00*   (2018.01)

(52) U.S. Cl.
   CPC .......... *G06Q 50/22* (2013.01); *G06F 19/00* (2013.01); *G06Q 10/10* (2013.01); *G16H 50/20* (2018.01)

(58) Field of Classification Search
   CPC ... A61B 5/0031; A61B 5/7275; A61B 5/0402; G06F 19/3418; G06F 15/42; G06Q 50/22; A61N 1/362

USPC ..... 600/300, 518, 513; 607/14, 32, 9, 30, 2; 700/83; 705/2, 3; 435/13
   See application file for complete search history.

(56) References Cited

U.S. PATENT DOCUMENTS

| | | | | |
|---|---|---|---|---|
| 6,243,606 B1* | 6/2001 | Mann et al. | ..................... | 607/14 |
| 6,400,996 B1* | 6/2002 | Hoffberg et al. | ............... | 700/83 |
| 6,497,655 B1* | 12/2002 | Linberg et al. | ................ | 600/300 |
| 6,804,558 B2* | 10/2004 | Haller et al. | ..................... | 607/30 |
| 6,980,851 B2* | 12/2005 | Zhu | ....................... | A61N 1/3627 600/513 |
| 7,072,802 B2* | 7/2006 | Hartlaub | ....................... | 702/188 |
| 7,096,064 B2* | 8/2006 | Deno et al. | ....................... | 607/9 |
| 7,155,277 B1* | 12/2006 | Brewer et al. | ..................... | 607/2 |
| 7,228,173 B2* | 6/2007 | Cazares | ............. | A61B 5/04525 600/509 |
| 7,277,747 B2 | 10/2007 | Cazares et al. | | |
| 7,738,950 B2* | 6/2010 | Johnson | ............. | A61B 5/02405 600/515 |
| 2002/0029002 A1* | 3/2002 | Bardy | ........................... | 600/518 |

(Continued)

OTHER PUBLICATIONS

Google patents search, Oct. 5, 2017.*
Google patents search, Jan. 16, 2019 (Year: 2019).*

*Primary Examiner* — Dilek B Cobanoglu
(74) *Attorney, Agent, or Firm* — Pauly, DeVries Smith & Deffner LLC

(57) ABSTRACT

This document discusses, among other things, systems and methods to enable physician labels on a remote server and use labels to verify and improve algorithm results. A method comprises using patient data in an automated analysis to obtain a result; receiving a message from the user, wherein the message is related to the result; and using at least a portion of the message to automatically modify the analysis.

21 Claims, 22 Drawing Sheets

(56) References Cited

U.S. PATENT DOCUMENTS

| | | |
|---|---|---|
| 2002/0107641 A1 | 8/2002 | Schaeffer et al. |
| 2002/0123672 A1* | 9/2002 | Christophersom et al. .. 600/300 |
| 2003/0004403 A1* | 1/2003 | Drinan et al. ................ 600/301 |
| 2003/0014282 A1* | 1/2003 | Haaksma et al. ................ 705/3 |
| 2005/0010258 A1* | 1/2005 | Peterson et al. ................ 607/32 |
| 2005/0151640 A1* | 7/2005 | Hastings ................ A61B 5/411 |
| | | 340/539.11 |
| 2005/0191716 A1* | 9/2005 | Surwit et al. ................... 435/13 |
| 2006/0025931 A1 | 2/2006 | Rosen et al. |
| 2006/0030890 A1 | 2/2006 | Cosentino et al. |
| 2006/0031094 A1* | 2/2006 | Cohen et al. ..................... 705/2 |
| 2006/0047538 A1* | 3/2006 | Condurso et al. ................ 705/3 |
| 2006/0049936 A1 | 3/2006 | Collins, Jr. et al. |
| 2007/0213599 A1 | 9/2007 | Siejko et al. |

* cited by examiner

RESULTS ARE:
| CORRECT | INCORRECT |

*FIG. 21*

METHOD AND SYSTEM TO ENABLE PHYSICIAN LABELS ON A REMOTE SERVER AND USE LABELS TO VERIFY AND IMPROVE ALGORITHM RESULTS

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2006, Cardiac Pacemakers, Inc. All Rights Reserved.

TECHNICAL FIELD

This patent document pertains generally to implantable medical devices, and more particularly, but not by way of limitation, to systems and methods for enabling physician labels on a remote server and using labels to verify and improve algorithm results.

BACKGROUND

Implantable medical devices (IMDs), including cardiac rhythm management devices such as pacemakers and implantable cardioverter/defibrillators, typically have the capability to communicate with an external device, such as an external programmer, via wireless telemetry, such as a radio-frequency (RF) or other telemetry link. While an external programmer is typically provided to program and modify the operating parameters of an IMD, modern IMDs also include the capability for bidirectional communication so that information, such as physiological data, can be transmitted to the programmer. Home health care remote monitoring systems can also communicate with the IMD and collect the patient and patient-related data. In addition, some monitoring systems can also collect other objective or subjective data using additional external sensors, such as a blood pressure cuff, a weight scale, or a specialized device that prompts the patient with questions regarding their health state. Some home health care monitoring systems can communicate with a centralized system, such as directly or using a networked system. Centralized systems, including medical practice systems, provide an efficient mode for physicians and other medical practitioners to manage patient-related data.

OVERVIEW

Example 1 describes a method comprising using patient data in an automated analysis to obtain a result; receiving a message from the user, wherein the message is related to the result; and using at least a portion of the message to automatically modify the analysis.

In Example 2, the method of Example 1 is optionally performed comprising: providing the result to a user; and receiving a response from the user, wherein the response is related to the result and wherein the response is include in the message.

In Example 3, the methods of any one or more of Examples 1 or 2 are optionally performed such that the response includes a verification message or a control message.

In Example 4, the methods of any one or more of Examples 1-3 are optionally performed such that the verification message indicates an accuracy of the result.

In Example 5, the methods of any one or more of Examples 1-4 are optionally performed such that the control message includes one or more parameters to improve the performance of the analysis.

In Example 6, the methods of any one or more of Examples 1-5 are optionally performed such that the parameters include one or more of: a threshold, an indication of a specificity, or an indication of a sensitivity.

In Example 7, the methods of any one or more of Examples 1-6 are optionally performed such that the message includes an assessment message, wherein the assessment message includes a result of an independent assessment of a patient, wherein the independent patient assessment is used to determine a result that is comparable to the result of the analysis.

In Example 8, the methods of any one or more of Examples 1-7 are optionally performed comprising receiving patient data at a central system.

In Example 9, the methods of any one or more of Examples 1-8 are optionally performed such that using patient data includes determining a patient condition.

In Example 10, the methods of any one or more of Examples 1-9 are optionally performed such that the message is formatted using a standardized interface language.

In Example 11, the methods of any one or more of Examples 1-10 are optionally performed such that the standardized interface language includes XML.

Example 12 describes a system comprising a patient device. The patient device comprises a communication module adapted to receive a message from the user, wherein the message is related to the result; and an analysis module adapted to: use patient data in an automated analysis to obtain a result; and use at least a portion of the message to automatically modify the analysis.

In Example 13, the system of Example 12 is optionally configured such that the communication module is further adapted to: provide the result to a user; and receive a response from the user, wherein the response is related to the result and wherein the response is include in the message.

In Example 14, the system of any one or more of Examples 12 or 13 are optionally configured such that the response includes a verification message or a control message.

In Example 15, the system of any one or more of Examples 12-14 are optionally configured such that the verification message indicates an accuracy of the result.

In Example 16, the system of any one or more of Examples 12-15 are optionally configured such that the control message includes one or more parameters to improve the performance of the analysis.

In Example 17, the system of any one or more of Examples 12-16 are optionally configured such that the parameters include one or more of: a threshold, an indication of a specificity, or an indication of a sensitivity.

In Example 18, the system of any one or more of Examples 12-17 are optionally configured such that the message includes an assessment message, wherein the assessment message includes a result of an independent assessment of a patient, wherein the independent patient assessment is used to determine a result that is comparable to the result of the analysis.

In Example 19, the system of any one or more of Examples 12-18 are optionally configured such that the communication module is included in at a central system.

In Example 20, the system of any one or more of Examples 12-19 are optionally configured such that the analysis module is further adapted to use the patient data to determining a patient condition.

Example 21 describes an apparatus comprising: means for using patient data in an automated analysis to obtain a result; means for receiving a message from the user, wherein the message is related to the result; and means for using at least a portion of the message to automatically modify the analysis.

This overview is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 21 is an example of a user-interface to allow a medical professional to submit input or feedback to a control system.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Overview

Figure 1:
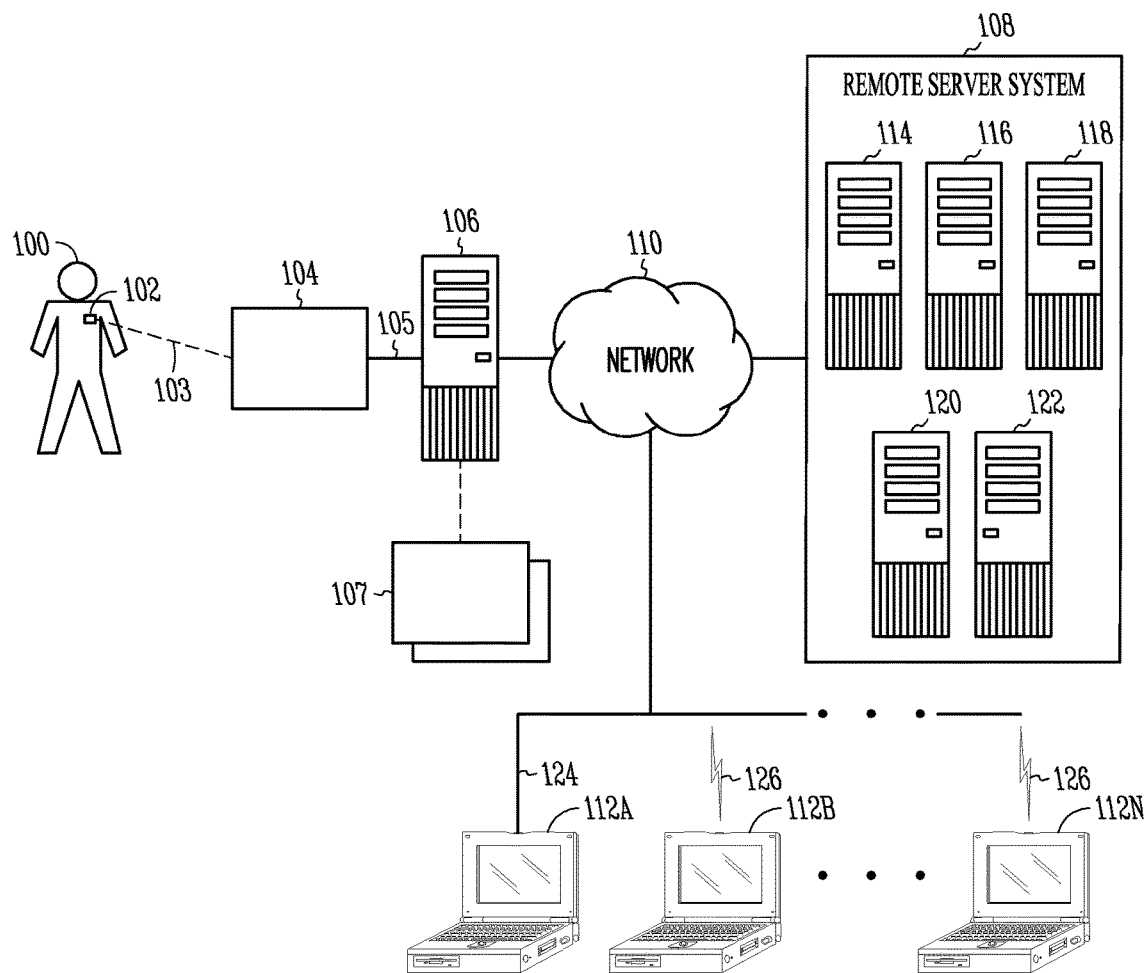
FIG. 1 illustrates portions of a system that enables physician-patient communication.

FIG. 1 illustrates portions of a system that enables physician-patient communication. In the example of FIG. 1, a patient 100 is provided with an implantable medical device (IMD) 102. Examples of implantable medical devices include a pacemaker, an implantable cardioverter defibrillator (ICD), a cardiac resynchronization therapy pacemaker (CRT-P), a cardiac resynchronization therapy defibrillator (CRT-D), a neurostimulation device, a deep brain stimulation device, a cochlear implant or a retinal implant. In some examples, the IMD 102 is capable of sensing physiological data and storing such data for later communication. Examples of physiological data include implantable electrograms, surface electrocardiograms, heart rate intervals (e.g., AA, VV, AV or VA intervals), electrogram templates such as for tachyarrhythmia discrimination, pressure (e.g., intracardiac or systemic pressure), oxygen saturation, activity, heart rate variability, heart sounds, impedance, respiration, intrinsic depolarization amplitude, or the like.

The IMD 102 is capable of bidirectional communication 103 with an external transceiver 104. In various examples, the IMD 102 receives commands from the transceiver 104 and may also communicate one or more patient indications to the transceiver 104. Examples of patient indications may include such things as heart rate, heart rate variability, data related to tachyarrhythmia episodes, hemodynamic stability, activity, therapy history, autonomic balance motor trends, electrogram templates for tachy discrimination, heart rate variability trends or templates, or trends, templates, or abstractions derived from sensed physiological data. In some examples, patient indications include one or more physiological indications, such as the physiological data described above. In another example, the IMD 102 may also communicate one or more device indications to the transceiver 104. Examples of device indications include lead/shock impedance, pacing amplitudes, pacing thresholds, or other device metrics. In certain examples, the IMD 102 may communicate sensed physiological signal data to the transceiver 104, which may then communicate the signal data to a remote device, such as for processing.

Typically, the transceiver 104 is located in close proximity to the patient 100. The transceiver 104 may be included within or attached to a personal computer or a specialized device, such as a medical device programmer. In one example, the transceiver 104 is a hand-held device that is capable of connecting to a local computer 106. Typically, a connection 105 can be made using a hard-wired connection (e.g., serial, USB, Firewire) or a wireless connection (e.g., RF, IR). In some examples, the local computer 106 is a specialized device or a personal computer. In certain examples, the local computer 106 is adapted to communicate with a remote server system 108. The communication link between the local computer 106 and the remote server system 108 is typically made through a computer or telecommunications network 110. The network 110 may include, in various examples, one or more wired or wireless networking such as the Internet, satellite telemetry, cellular telemetry, microwave telemetry, or other long-range communication networks.

In an example, one or more external sensors 107 are adapted to communicate with the transceiver 104 and may transmit and receive information, such as sensed data. External sensors 107 may be used to measure patient physiological data, such as temperature (e.g., a thermometer), blood pressure (e.g., a sphygmomanometer), blood characteristics (e.g., glucose level), body weight, physical strength, mental acuity, diet, or heart characteristics. An external sensor 107 may also include one or more environmental sensors. The external sensors 107 can be placed in a variety of geographic locations (in close proximity to patient or distributed throughout a population) and can record non-patient specific characteristics such as, for example, temperature, air quality, humidity, carbon monoxide level, oxygen level, barometric pressure, light intensity, and sound.

External sensors 107 can also include devices that measure subjective data from the patient. Subjective data includes information related to a patient's feelings, perceptions, and/or opinions, as opposed to objective physiological data. For example, the "subjective" devices can measure patient responses to inquiries such as "How do you feel?", "How is your pain?" and "Does this taste good?" Such a device may also be adapted to present interrogatory questions related to observational data, such as "What color is the sky?" or "Is it sunny outside?" The device can prompt the patient and record responsive data from the patient using visual and/or audible cues. For example, the patient can press coded response buttons or type an appropriate response on a keypad. Alternatively, responsive data may be collected by allowing the patient to speak into a microphone and using speech recognition software to process the response.

In some examples, the remote server system 108 comprises one or more computers, such as a database server 114, a network server 116, a file server 118, an application server 120 and a web server 122. In certain examples, one or more terminals 112A, 112B, . . . , 112N are locally or remotely connected to the remote server system 108 via network 110. The terminals 112 are communicatively coupled to the remote server system 108 using a wired 124 or a wireless connection 126. Examples of terminals 112 may include personal computers, dedicated terminal consoles, handheld devices (e.g., a personal digital assistant (PDA) or cellular telephone), or other specialized devices. In various examples, one or more users may use a terminal 112 to access the remote server system 108. For example, a customer service professional may use a terminal 112 to access records stored in the remote server system 108 to update patient records. As another example, a physician or clinician may use a terminal 112 to receive or provide patient-related data, such as comments regarding a patient visit, physiological data from a test or collected by a sensor or monitor, therapy history (e.g., IMD shock or pacing therapy), or other physician observations.

In some examples, the IMD 102 is adapted to store patient data and to use the data to provide tailored therapy. For example, using historical physiological data, an IMD 102 may be able to discriminate between lethal and non-lethal heart rhythms and deliver an appropriate therapy. However, it is often desirable to establish a proper baseline of historical data by collecting a sufficient amount of data in the IMD 102. In some examples, a "learning period" of some time (e.g., thirty days) is used to establish the baseline for one or more physiological signals. An IMD 102 may, in an example, store a moving window of data of operation, such as a time period equal to the learning period, and may use the information as a baseline indication of the patient's biorhythms or biological events.

Once the baseline is established, then acute and long-term patient conditions may be determined probabilistically. The baseline may be established by using historical patient records or by comparing a patient to a population of patients. In an example, a diagnostic technique uses a patient-based baseline to detect a change in a patient's condition over time. Examples of a diagnostic technique that uses a patient-derived baseline are described in the next section.

In an example, patient diagnostics are automatically collected and stored by the implanted device 102. These values may be based on the patient's heart rate or physical activity over a time period (e.g., 24-hour period) and each diagnostic parameter is saved as a function of the time period. In one example, heart-rate based diagnostics utilize only normal intrinsic beats. For heart rate variability (HRV) patient diagnostics, the average heart rate can be found at each interval within the time period, for example, at each of the 288 five-minute intervals occurring during 24 hours. From these interval values, the minimum heart rate (MinHR), average heart rate (AvgHR), maximum heart rate (MaxHR) and standard deviation of average normal-to-normal (SDANN) values may be calculated and stored. In one example, the implanted device 102 computes a HRV Footprint® patient diagnostic that can include a 2-dimensional histogram that counts the number of daily heartbeats occurring at each combination of heart rate (interval between consecutive beats) and beat-to-beat variability (absolute difference between consecutive intervals). Each histogram bin contains the daily total for that combination. The percentage of histogram bins containing one or more counts can be saved each day as the footprint percent (Footprint %). The implanted device 102 can also provide an Activity Log® patient diagnostic (Activity %), which can include a general measure of patient activity and can be reported as the percentage of each time period during which the device-based accelerometer signal is above a threshold value.

Within-Patient Diagnosis

In certain examples, a within-patient diagnostic technique measures short-term variance of one or more patient-related physiological parameters to detect acute changes in physiologic sensor values. The measured physiological parameters may be compared to a baseline value to detect changes that exceed a threshold value. These changes may occur within a short period before a patient experiences an onset of a physiological condition and as such, an alert may be generated when changes exceed the threshold amount.

Figure 2:
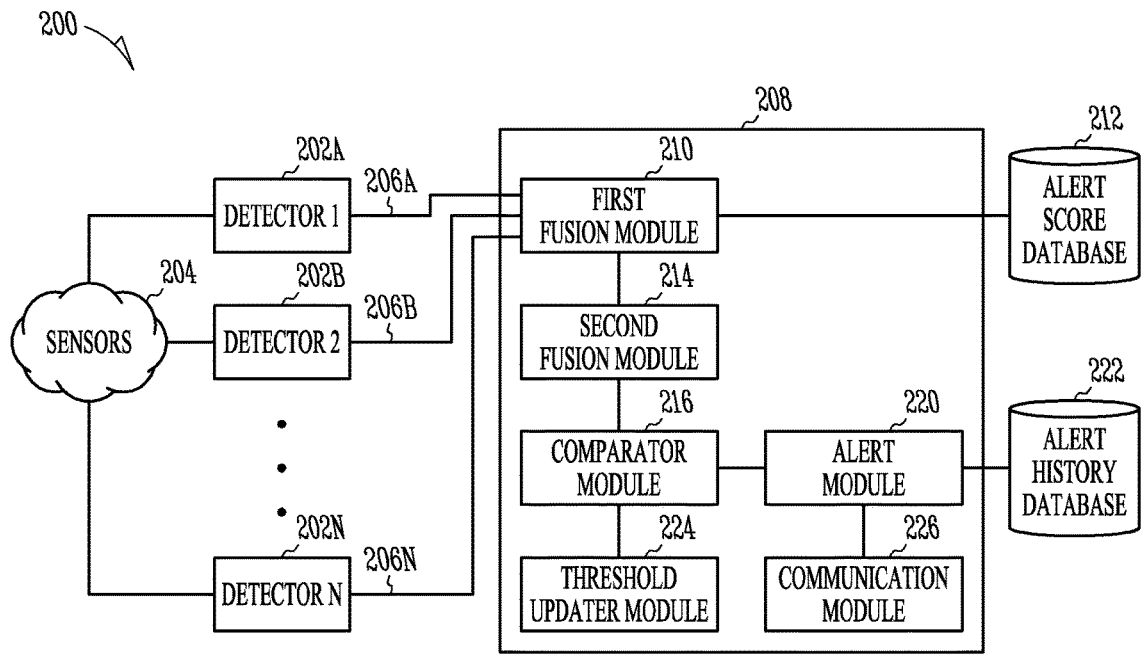
FIG. 2 is a detailed schematic view illustrating portions of a system that measures and detects variance in patient-related data to identify acute changes that may indicate an onset of a physiological condition.

FIG. 2 is a detailed schematic view illustrating portions of a system 200 that measures and detects variance in patient-related data to identify acute changes that may indicate an onset of a physiological condition. In the system 200, two or more detectors 202A, 202B, . . . , 202N are connected to one or more sensors 204. Sensors 204 may include implanted or external sensors, such as those described above. Sensors 204 may be configured to automatically collect patient-related data (e.g., a heart rate monitor) or be configured to operate by user commands (e.g., an interrogatory device with a display, or a weight scale). The patient-related data may include sensed physiological data, sensed environmental data, or data collected from a patient in response to a query or request. Examples of the sensors 204 include, without limitation, an electrocardiogram, an accelerometer, a pressure sensor, a cardiac output (CO) detector, a heart rate monitor, an interrogatory device, a weight scale, and a microphone. Examples of sensed value include, without limitation, standard deviation of averaged normal-to-normal (SDANN) cardiac depolarization interval trends, heart rate minimum (HRMin), physical activity, or a patient compliance index (as described below). Each detector 202 may include hardware or software to evaluate the one or more input signals from the one or more sensors 204, such as to determine a value of an alert status associated with the sensor-detector pair.

Detectors 202 may be configured to provide an alert status when one or more conditions are detected. In an example, the alert status is based on comparing one or more parameters (e.g., sensed values) to one or more threshold values, such as to determine whether the one or more parameters exceeds or falls below its corresponding threshold value. Threshold values may be configured as an absolute value (e.g., a minimum or maximum acceptable safety value) or based on a difference or change from a baseline or other known value. For example, a threshold may be configured as a maximum (or minimum) percent change from a value (e.g., baseline value); as a standard deviation value from a value; or an absolute change from a value (e.g., an increase of five points). In an example, the maximum percent change threshold value is computed by using a baseline value, such that if the sensed value (or daily average of sensed values) exceeds the percent change threshold from the baseline value an alert status is found. Baseline values may be calculated using a central tendency (e.g., average, mean, median, mode, etc.) or other composite of two or more sensed values over a particular time period (e.g., day, week, month, training period, etc.). An initial threshold value may be determined using performance of the within-patient diagnostic technique during a training or learning period (e.g., the first 30 days of operation of a new device). One or more threshold values may be adjusted, automatically or manually, from the initial threshold value during later performance.

In some examples, an alert status is reflective of whether an event occurred. For example, if a patient is requested to perform an action (e.g., take medicine or exercise daily) and fails to perform the requested action, then an alert may be generated. In various examples, the alert status may be represented as a binary value, a substantially continuous value, or a discrete value. Binary values may represent, for example, whether a patient action was detected (e.g., yes/no) or whether a two-state condition exists (e.g., on/off, hot/cold). Additionally, binary values may indicate whether a patient is more or less likely to experience a health change, such as a change to quality of life, an onset of a disease state (e.g., heart failure decompensation), or death. Discrete values may indicate, for example, a multi-state condition (e.g., low/medium/high) or a scaled value, such as a subjective rating of pain on a scale of one to five. Substantially continuous values may indicate, for example, a normalized scale, such as a scale of zero to one, however, such values may be quantized by an analog-to-digital converter.

Each alert status is communicated to a fusion machine 208 using a corresponding data pathway 206A, 206B, . . . , 206N. Depending on the configuration of the detectors 202 and the fusion machine 208, one or more of the corresponding data pathways 206 may be wired or wireless. For example, in certain examples, the detectors 202 and the fusion machine 208 are integrated into an IMD. In other examples, one or more detectors 202 may be located separate from the IMD and possibly separate from each other. In this case, the fusion machine 208 may be integrated into one or more detectors 202 or it may comprise a separate machine.

Moreover, although the example illustrated in FIG. 2 depicts a detector 202 associated with an alert status value (communicated over a data pathway 206), sensors 204, detectors 202, and data pathways 206 may be combined or multiplexed in various ways. For example, a detector 202 may use one or more sensors 204 to determine an alert status value. As another example, two or more detectors 202 may be used in combination to determine a particular alert status value. In another example, sensors 204 or detectors 202 may be reused in multiple combinations or permutations with other sensors 204 or detectors 202 to derive alert status values. Such combinations or permutations of sensors 204 or detectors 202 may be advantageous to provide an alert status value that reflects a more complex decision or determination.

The two or more detectors 202 may communicate their alert status values to a first fusion module 210. The first fusion module 210 calculates an alert score using the alert status from one or more detectors 202. In an example, the first fusion module 210 uses a weighted function to calculate the alert score. The weights in the weighted function may be adapted for a particular patient or a particular population of patients, such as by adjusting the weights based on prior knowledge of the suspected patient condition and the types or numbers of sensors used. For example, patients at high risk of heart failure decompensation may exhibit an unusually low physical activity or heart rate variability (HRV). By increasing the sensitivity of these sensors (e.g., decreasing a threshold value), a lower physical activity value or a lower HRV value may be detected earlier.

In another example, weights in the weighted function may be based on time, the number or types of sensors, or a confidence value associated with a sensor 204 or detector 202. For example, more recent alert values may be weighed more than less recent alert values; a particular type of sensor may be considered more reliable and assigned a comparatively higher weight than sensors considered less reliable. As another example, in a situation where more than one sensor is used to determine an alert value, the number of sensors used to determine such an alert status may be used to assign a weight, such that alert values calculated using more sensors may be considered more reliable and thus, have a higher weight compared to alert values calculated using fewer sensors. In yet another example, weights may be assigned using a cost function. For example, individual decisions could be weighted according to their reliability, such that the weights may be regarded as a function of the probability of miss or the probability of false alarm of an individual detection.

In addition, weights may be modified, such as between alert score calculations, to adaptively adjust to changing conditions. The alert score may be calculated periodically or recurrently, such as hourly, daily, or weekly. In an example, after calculating the alert score, the first fusion module 210 stores the alert score in an alert score memory 212. The history of alert scores may be used to track changes or in further processing, as described below. The alert score memory 212 may include a database, files, random access memory, or other storage unit.

The alert score may be communicated from the first fusion module 210 to the second fusion module 214. In another example, the second fusion module 214 accesses a storage unit, such as the alert score database 212, to obtain the current alert score. The second fusion module 214 also accesses the same or a different storage unit to obtain one or more historical alert scores. In an example, a fixed number of historical alert scores are obtained from the storage unit, such as to obtain a "moving window" of the most recent historical alert score data. For example, when alert scores are calculated and stored weekly, then three prior calculated alert scores may be obtained, along with the current alert score, to effectively view a month's worth of alert score data. The second fusion module 214 uses the one or more historical alert scores in combination with the current alert score to calculate a combined alert score (CAS). In an example, the CAS is a weighted function of the alert scores. In various examples, weights in the weighted function may be equal, unequal, adaptive based on one or more patient characteristics, or based on time (e.g., more recent alert scores are given a higher weight, being considered more relevant, while less recent alert scores are given a lower weight).

In an example, the second fusion module 214 communicates the CAS to a comparator module 216. The comparator module 216 compares the CAS to a threshold CAS value. In various examples, the threshold CAS value is an absolute value, or may be based on a percent change from a baseline or other standard value. In other examples, the threshold CAS value is dynamic or static. For example, the threshold CAS value may be manually set by a user. The user may change the value at recurrent or periodic intervals. For example, a user may set the CAS threshold to some arbitrary high value and then dynamically or manually adjust the CAS threshold, such as to fine tune false positive or false negative rates (e.g., specificity or sensitivity).

Sensitivity generally refers to the ability of the detection scheme to effectively detect a particular result. Sensitivity can be expressed with the formula: sensitivity=(true positives)/(true positives+false negatives). Thus, a higher sensitivity generally indicates that an analysis correctly characterizes more true positives or eliminates false negatives.

Specificity generally refers to the ability of the detection scheme to avoid improper classifications. Specificity can be expressed with the function: specificity=(true negatives)/(true negatives+false positives). Thus, a higher specificity generally reflects more accurate classification of true negatives or reduction of false positives.

In other examples, the threshold CAS value is determined automatically. In an example, the threshold updater module 224 uses one or more input parameters to configure or update the threshold CAS value. Input parameters may include things such as the time, the number of sensors or detectors, one or more patient characteristics, a physician's or clinician's preference, the previous threshold CAS value, or the CAS. The threshold updater module 224 may communicate the current threshold value to the comparator module 216 for use in the comparison. In certain examples, the threshold CAS value is established using a constant false alarm rate (CFAR) technique, such as described in Siejko et al U.S. patent application Ser. No. 11/276,735, entitled PHYSIOLOGICAL EVENT DETECTION SYSTEMS AND METHODS, filed on Mar. 13, 2006, which is assigned to the assignee of the present patent application, and which is incorporated herein by reference in its entirety, including its description of CFAR event detection techniques.

When the CAS exceeds the threshold CAS value, then the comparator module 216 provides an indication of this state to the alert module 220. The alert module 220 may, in some examples, record one or more aspects of the generated alert, such as in alert history database 222. The alert module 220 may communicate the alert state to a communication module 226, for communication to a user (e.g., a physician or clinician).

While FIG. 2 illustrates an example of a system 200 that implements fusion logic in a fusion machine 208, portions of the processing may occur at the sensor 204, detector 202, or be distributed among several processing machines. For example, a sensor 204 or detector 202 may include memory to record one or more sensed values over time and may only transmit a central tendency (e.g., mean, median, or mode) to the first fusion module 210 for further processing. As a further example, the fusion machine 208 may be located at a central server, programmer, or patient device.

Figure 3:
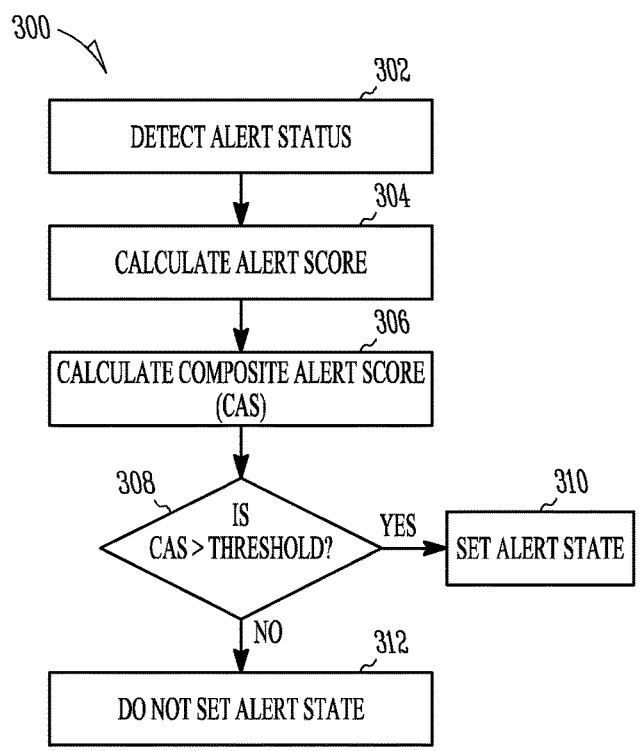
FIG. 3 illustrates a method of using a composite alert score to detect an increased likelihood of a disease state or onset of a physiological condition.

FIG. 3 illustrates a method 300 of using a composite alert score to detect an increased likelihood of a disease state or onset of a physiological condition. At 302, one or more alert status values are detected. Alert status values may be binary (e.g., on/off, yes/no, high/low), substantially continuous (e.g., 1.4, 2.9, 9.34) or discrete (e.g., 1 out of 5, 2 out of 4). At 304, an alert score is calculated using the alert status values. In an example, the alert score is a weighted function, such that:

$$\text{Alert Score}(AS) = \text{Alert}_1 * w_1 + \text{Alert}_2 * w_2 + \ldots + \text{Alert}_m w_m$$

where weights $w_1, w_2, \ldots, w_m$, may be modified to weigh one alert value higher or lower than another alert value based on a factor, such as a patient characteristic or a sensor confidence level. In an example, alerts may be temporally related. For example, an alert status may be detected on a periodic or recurrent basis, such as daily, from a particular sensor. In another example, alerts may be otherwise associated. For example, alert statuses may be detected from one or more of similar types of sensors (e.g., implanted and external heart rate monitors), such that if an alert is detected from one sensor, then the alert may be considered to be active for all related or associated sensors. In another example, all related or associated sensors are polled and an alert is detected when some plurality or all concur on an alert state.

At 306, two or more alert scores are combined into a composite alert score (CAS). In an example, the CAS is a weighted function of alert scores, such that:

$$\text{Composite Alert Score}(CAS) = AS_i * w_i + AS_{i-1} * w_{i-1} + \ldots + AS_n * w_n$$

where weights $w_i, w_{i-1}, \ldots, w_n$ may be modified to weigh one alert score higher or lower than another alert score based on a factor, such as time, patient changes over time, or the like. In an example, $AS_i$ is the alert score of the current period and $AS_{i-1}$ is the alert score for the previous period, etc. Periods may be days, weeks, months, or some other regular time interval. At 308, the CAS is compared to a threshold value. In an example, the threshold is fixed, however it may be adapted, such as for particular patients or over time in other examples. When the CAS is over the threshold value in this example, then at 310, an alert state is set. If the CAS does not exceed the threshold value in this example, then at 312, the alert state is not set. In various examples, the alert state may indicate one or more of an onset of a physiological condition, a change in a physiological condition, or a predictive measure of a possibility of an onset of such a physiological condition. For example, the alert state may be used to assist in predicting physiological or patient-related events, such as HF decompensation, lead fracture, sudden cardiac death (SCD), or myocardial infarction (MI). Additionally, the alert state may be indicative of or used for determining a likelihood of a change in a patient's quality of life or a likelihood of patient death in a particular time period or time frame. Portions or all of the method 300 may be executed on different processing machines, for example, method 300 could be executed by a central server, a programmer, or a patient device.

Figure 4:
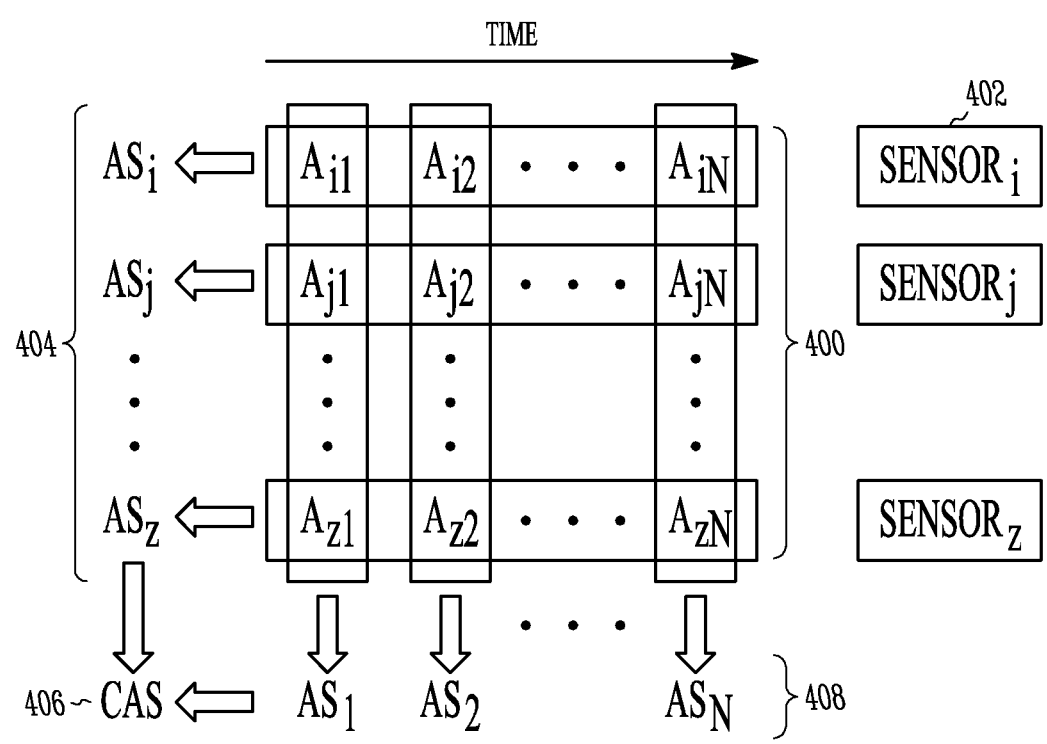
FIGS. 4-6 are diagrams illustrating examples of relationships between alert values, alert scores, and composite alert scores.

FIG. 4 is a diagram illustrating an example of relationships between alert values, alert scores, and composite alert scores. In an example, alert values 400 are sensed or detected over time and associated with a particular sensor 402. Alert values 400 may be combined first with respect to a particular sensor 402, for example, $AS_i, AS_j, \ldots, AS_z$ 404. The alert scores combined with respect to each sensor may then be combined to form the composite alert score, CAS 406. Alternatively, alert values 400 may be combined first with respect to a particular time slice, such that $AS_1$, $AS_2, \ldots, AS_N$ 408. Similarly, the alert scores combined with respect to each particular time slice may then be combined into a composite alert score 406. As described above, the calculation of the alert scores, either with respect to a particular sensor or with respect to a particular time slice, may include the use of a weighted function. In addition, the calculation of the combined alert score 406 may include a weighted function.

Figure 5:
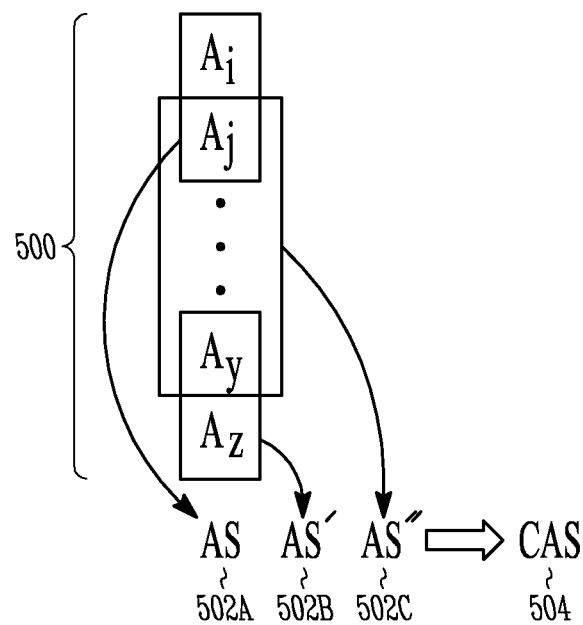
Figure 6:
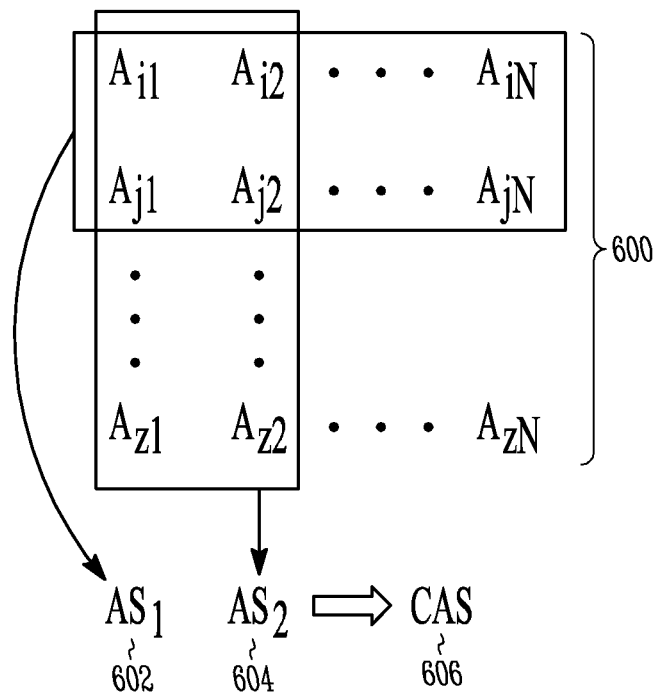

In other examples, as illustrated in FIGS. 5-6, alert scores may be calculated using various combinations of alert values. FIG. 5 is a diagram illustrating relationships between alert values, alert scores, and composite alert scores. In FIG. 5, alert values 500 are used in various combinations to determine alert scores 502A, 502B, 502C. For example, alert score AS 502A is composed of alert values $A_i$ and $A_j$, alert score AS' 502B is composed of alert values $A_y$ and $A_z$, and alert score AS" 502C is composed of alert values $A_j$ and $A_y$. Alert scores 502A, 502B, 502C may be combined to form a composite alert score 504. Alert values 500 may be obtained from the same sensor over time or from two or more sensors. In an example, when alert values 500 are obtained from the same sensor, the alert values 500 may be determined at periodic or recurring time intervals, such as daily, hourly, or the like. In another example, when alert values 500 are obtained from two or more sensors, the values 500 may be obtained at approximately the same time.

FIG. 6 illustrates another relationship between alert values, alert scores, and composite alert scores. Provided an array or matrix of alert values 600, various subsets of alert values 600 may be combined to form alert scores, such as $AS_1$ 602 and $AS_2$ 604. Alert scores 602, 604 may be combined to form a composite alert score 606. As described above with reference to other examples, relationships illustrated in FIGS. 5 and 6 may include weighted functions.

Surrogate Measure of Patient Compliance

Measurements of patient compliance may provide a general indication of how closely a patient follows a physician's or clinician's direction or instruction. Patients who are non-compliant in one or more ways, such as concerning diet, exercise, or medicine, may also be non-compliant with regard to other medical advice or instruction. Non-compliant patients may benefit from closer observation or follow-up by their physician or clinician. The observation or follow-up may assist the physician or clinician in managing an increased medical risk due to non-compliance and increasing the patient's overall compliance. In addition, non-compliant patients may benefit from re-evaluating, modifying, ceasing, or implementing new therapies.

In some examples, patient compliance may be measured by detecting whether one or more requested actions were performed by the patient. Performance may be analyzed using one or more indexes, such as with respect to frequency, time, or technique or the like. For example, a patient who is requested to weigh himself unclothed daily at 9:00 AM may have a high frequency compliance score if he consistently weighs himself every day. However, if the weigh-ins are sporadically timed, for example from 8:30 AM to 11:00 AM, then the patient may be associated with a relatively lower time compliance score. In addition, if the patient's weight measured during weigh-ins differs by more than a few pounds, which may be considered normal daily weight variance, then it may be deduced that the patient was clothed during some weigh-ins and thus, may be associated with a relatively lower technique compliance score.

Thus, frequency compliance may be measured by a frequency compliance index score, and can be conceptualized as how often the requested action is documented. In an example, the frequency compliance score is measured as a ratio of missed measurements over a particular time period. In such a configuration, a higher frequency compliance score may indicate a lower patient compliance. In another example, an inverse ratio is used, that is, the number of successful measurements over a particular time period, where a higher compliance score may indicate a more patient compliance.

In addition, time compliance can be conceptualized as when an action is performed or documented, such as what time of day or what day of week. Time compliance may be measured by a time compliance index score. In an example, a variance or standard deviation or other measure of variability of the time of performance with respect to the requested time is calculated over a time period. In such a configuration, a higher variability score may indicate less patient compliance. The time compliance index score may be a function of such a variability score, such as a normalized inverse of the variability score such that a higher time compliance index score indicates a generally more compliance patient.

Technique compliance may be viewed as how correctly or how completely a patient conducts or performs a requested action. By using one or more objective auxiliary measurements, a technique compliance index score may be derived. Not every requested patient action may be tested for technique compliance as some actions are too simple and others do not provide objective metrics to measure technique.

Patient actions may be detected using an interactive or interrogatory device (e.g., a patient monitor or personal computer), one or more external devices (e.g., a weight scale or blood-pressure cuff), one or more implanted devices (e.g., a cardiac rhythm management (CRM) device, accelerometer, or heart monitor), or any combination thereof. Additional examples of external sensors include, but are not limited to, a peak flow monitor, a glucose monitor, an oxygen saturation monitor, or an electrocardiogram monitor.

Requested patient actions may include one or more actions related to ongoing health care or therapy. For example, a patient may be requested to measure their blood pressure or weight at regular intervals. Requested patient actions may also include non-health care or non-therapy related actions. For example, a patient could be requested to report the outside temperature daily at a particular time. Such an action is not directly related to a patient's health care or therapy, but may be used as a surrogate or indirect measure of compliance. Patients who are generally more compliant to arbitrary instructions may also be more compliant to health care directives.

Monitoring one or more patient compliance index scores may provide an indication of a change in physiological or psychological disease state. Patients may be compared to a population of patients to determine whether they fall outside a particular level of compliance or range of compliance index scores (e.g., a median or mode of a patient population). The population of patients may be selected using one or more of the patient's particular characteristics, such as age, weight, gender, disease risk, current medical status, or the like. In addition, patient compliance scores may be used in auxiliary processes, such as a within-patient diagnosis, as described above. An acute change in a patient's compliance over time may indicate the onset of a physiological or psychological condition or disease state, such as heart failure decompensation, as an illustrative example. In other examples, a change in a patient's compliance may be indicative of or used for determining a likelihood of a change in a patient's quality of life or a likelihood of patient death in a particular time period or time frame.

A patient may be characterized into a class of compliancy. Grouping patients that are generally more compliant and patients that are generally less compliant may be used to determine which patients may require more observation, clearer instruction, or different therapy.

Another use of surrogate measures of patient compliance is to identify or label data as outliers. In other words, collected patient data, which may include subjective response data, measured physiological data, or other detected, measured, or sensed data related to a patient, may be considered suspect or viewed with less confidence if the patient's surrogate measure of patient compliance is below a threshold acceptable level. In an example, patient data (e.g., electrograms, physical activity levels, HRV, heart sounds, etc.) recorded around the same time that the patient compliance score was below a threshold is flagged. Flags may be used as a measure of the quality of the measured patient data. For example, a patient compliance index score may be based on timely and consistent patient weigh-ins using an external weight scale. When the compliance index score falls below a threshold, patient weight values obtained may be considered suspect and may be weighted less in a within-patient or between-patient analysis. In another example, when the compliance index score falls below a threshold, physiological sensor data may instead be given an increased weight on the grounds that poor compliance can inferentially indicate that the patient may not be feeling well. This may be useful, for example, when the particular physiological sensor data is believed to be relatively independent of the particular patient compliance assessment technique being used.

Figure 7:
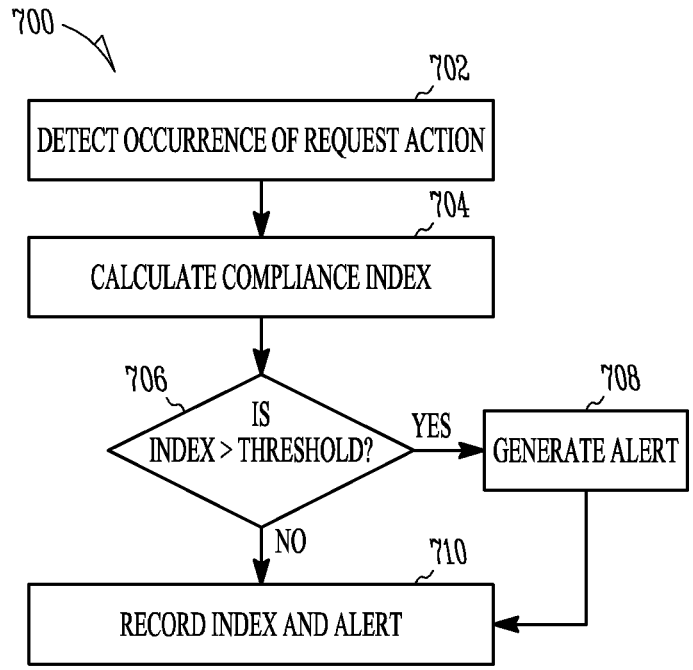
FIG. 7 illustrates an example of a method of using sensed patient actions to determine a level of patient compliance.
Figure 8:
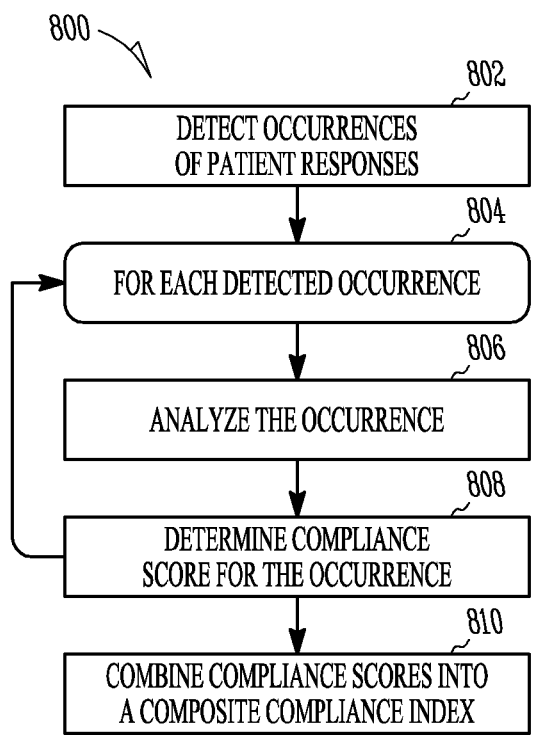
FIG. 8 illustrates an example of a method of determining a compliance index over two or more different patient responses.

Several modes of analysis are illustrated in FIGS. 7 and 8. FIG. 7 illustrates an example of a method 700 of using sensed patient actions to determine a level of patient compliance. The method 700 illustrated in FIG. 7 detects and monitors patient actions in response to a request. At 702, one or more occurrences of a patient action are detected. Patient actions may be in response to a request for such an action by a clinician, therapist, or physician. For example, a patient may be requested to log onto a website daily and answer one or more questions, which need not be related to the patient's health or current therapy. When a clinician asks a non-patient health related question, such as "Is it cloudy outside?", the clinician may be more interested in whether the patient responded, and when the patient responded, than whether the response is correct. In another example, a patient may be requested to take and report their blood pressure daily. Such a request may be related to the patient's current therapy or health monitoring, but for the purposes of measuring and determining patient compliance, the value of the blood pressure reading is irrelevant—the requesting physician or clinician may be more interested in the regularity or proper performance of the patient's actions. Some requested actions may be relatively simple, such as pressing a button on a user-interface display daily at a particular time. Other requested actions may be more complex, such as for example, accessing and interacting with a particular website.

At 704, a patient compliance index is calculated. In an example, the patient compliance index is calculated using one or more of a frequency compliance value, a time compliance value, or a technique compliance value. In an example, the patient compliance index is normalized, such as to provide a range of values from zero (least compliant)

to one (most compliant). In some examples, the patient compliance index is calculated using two or more values in a weighted function. In an example, the weighted function is a function of an aspect of a detected responsive patient action. For example, the weighted function may focus on the time compliance of the patient's actions over a period of time. The weighted function may weigh more recent occurrences more than less recent occurrences. In another example, the weighted function is a function of two or more aspects of a detected responsive patient action. For example, given a patient action, time compliance may be considered more important and thus given a higher weight in the weighted function than technique compliance. In another example, different weights are distributed both temporally and across different aspects of a detected patient action. Weight factors may also be related to the number or type of sensors used, one or more patient characteristics (e.g., health trends or risk stratification), or a patient population, in various examples.

At 706, the patient index is compared to one or more threshold values. In various examples, the threshold values may be an absolute value, a trended value, a population-based value, or the threshold value may be manually selected, e.g., by a user, such as a physician. Threshold values may define a minimum or maximum expected value, such that when the patient falls under a minimum threshold or exceeds a maximum threshold value, a resulting particular action or state (e.g., an alert or alarm) may occur. Threshold values may also be used to define an inner or outer range of expected or accepted values. For example, At 708, if the patient index violates a threshold value or condition, for example when a value is outside of a range bounded by one or more threshold values, then an alert is generated. The alert may be communicated to a user, such as a physician, or be used in further processing, such as in determining an alert score or a composite alert score, as described above.

The index score and one or more details about the alert state, e.g., whether an alert was generated, to whom it was communicated if there was an alert, etc., can also be stored at 710. The compliance index or alert may be provided to one or more other systems, processes, or devices, for example to record and maintain a patient history or for quality assurance evaluation of the system. Recording patient compliance index scores over a period of time may be advantageous to analyze or evaluate one or more trends in the patient's compliance activity.

While FIG. 7 illustrates a method 700 that emphasizes detecting and monitoring a single type of requested patient response, FIG. 8 illustrates an example of a method 800 of determining a compliance index over two or more different patient responses. In addition to being an indicator of patient compliance, monitoring more than one patient response may be advantageous, such as to determine a secondary physical, physiological, or psychological condition. For example, a patient may be requested to weigh themselves daily and also to report the outdoor temperature using a handheld interrogatory device (e.g., a patient monitoring device). When the patient fails to weigh themselves over several days, but continues to report the outdoor temperature using the handheld interrogatory device, it may be inferred by the attending physician that the patient may be physically unable to get to the bathroom to weigh himself. The inference may be supported by a deduced fact that the patient is still capable of reporting the temperature from using the handheld patient monitoring device, which may be situated more conveniently, such as beside the patient's bed. In such a situation, the physician may wish to follow up to ensure that the patient is physically stable. Detecting the presence or absence of data or other trends may be useful to determine or predict patient problems, such as heart failure decompensation, loss of cognitive function, or physical incapacity.

At 802, two or more occurrences of different patient responses are detected. Detection may be automatic or manual. Examples of an automatically detected patient response includes using a software program or other programmable device to telephone or email a patient daily at a particular time and detect a patient response. Other examples include sensors in implanted or external devices to detect things, such as physical activity levels of the patient, physical location of the patient (e.g., using a GPS device to detect whether the patient has left their house in a particular time period), or the like. Examples of manual detection include requesting that a patient measure themselves daily, such as by using a network-enabled weight scale connected to a centralized patient management system, or having a live operator or other personnel call or visit the patient daily to determine whether the patient was compliant that day.

At 804, for detected occurrences, the occurrence is analyzed at 806. Analysis of the occurrence may be similar to that described with reference to method 700 in FIG. 7. For example, one or more aspects of the occurrence may be analyzed, such the time regularity, frequency regularity, or technique correctness.

At 808, a compliance score is determined for the particular occurrence. The compliance score may be a weighted function of one or more aspects of the occurrence. The compliance score may also be a weighted function over time, such as weighing several successive occurrences in a particular time period.

At 810, the compliance scores of the two or more occurrences of different patient responses are combined into a composite compliance index. The composite compliance index may be computed using a weighted function. The weights in the weighted function may be static or dynamic. The composite compliance index may be stored and provided to other systems, processes, or devices.

Figure 9A:
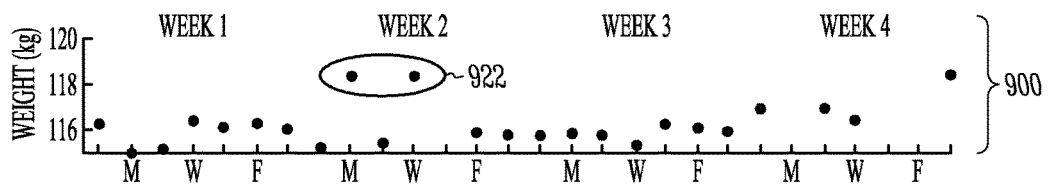
FIGS. 9A-9F are charts illustrating examples of recorded patient actions in response to at least one specific request.

FIGS. 9A-9F are charts illustrating examples of recorded patient actions in response to at least one specific request. In the example illustrated, the specific request is for the patient to weigh himself daily unclothed at 7:30 AM. The first chart 900 in FIG. 9A illustrates conceptualized (not real) data illustrating a series of weight measurements detected in response to the specific request. As illustrated, the patient's normal weight is in a range of approximately 114 kg and 117 kg. In an example, an allowable daily weight variance is provided to account for natural weight changes.

Figure 9B:
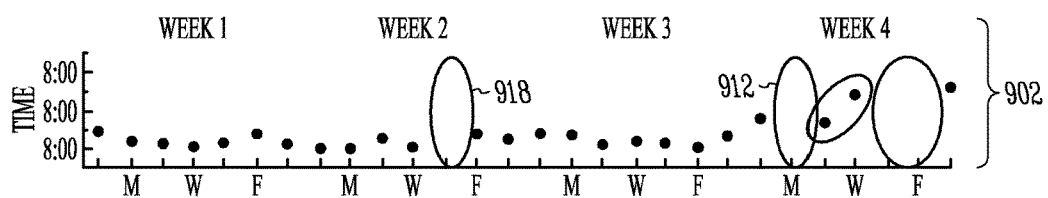

The second chart 902 in FIG. 9B illustrates the recorded time of each weigh-in. In an example, an allowable time variance is provided to allow for some flexibility in the timing of the patient's responsive action. In another example, any variance from the exact specified time may result in a lower compliance score.

Figure 9C:
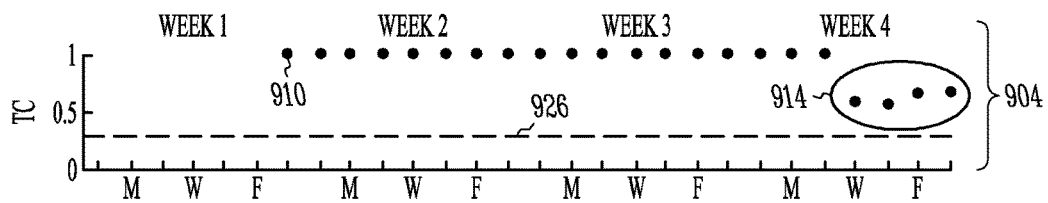
Figure 9D:
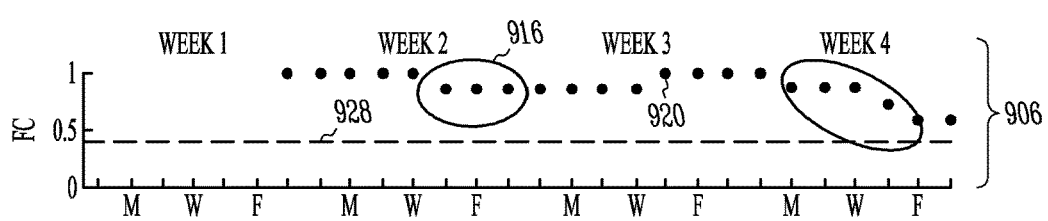
Figure 9E:
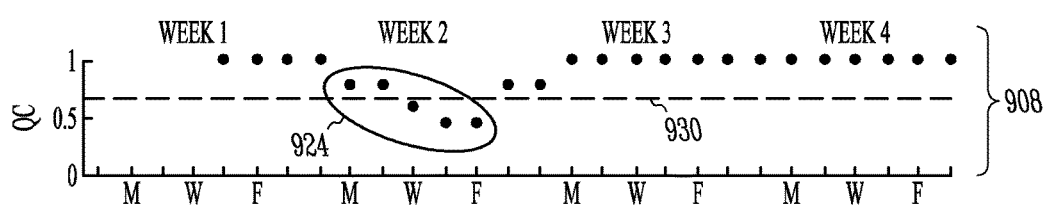

The third, fourth, and fifth charts 904, 906, 908 illustrated in FIGS. 9C-9E respectively illustrate a trended time compliance score, a trended frequency compliance score, and a trended quality compliance score (technique compliance). In an example, the trended time compliance score, as illustrated in the third chart 904, is computed using the previous week's worth of recorded patient actions. In an example, the trended time compliance score is normalized, such as from a score of zero to one. Here, the specified time to perform the action is 7:30 AM. Using an allowable time variance of ±30 minutes in this example, when a patient perform the requested action (weighing in) at any time between 7:00 AM and 8:00 AM, the patient is deemed to be in full compliance with respect to time. Using the prior seven day's data, the first value 910 of trended time compliance is a 1.0 because each of the prior seven day's weigh-ins were performed within the 7:00 AM to 8:00 AM allowable time range. When the patient fails to perform the requested action within the allowable range, such as at 912, then the corresponding trended time compliance score falls, such as at group 914.

The fourth chart 906 in FIG. 9D illustrates a trended frequency compliance score based on the data in the first chart 900. Similar to the time compliance scores, the trended frequency compliance score is based on the previous week's worth of data, in an example. Here, when the patient performs the action, a corresponding daily frequency compliance score is one, and when the patient fails to perform the action, the corresponding daily frequency score is zero. The trended frequency compliance may be calculated as a linear function of the previous week's daily frequency compliance scores, such as $$\frac{\sum_{j=0}^{6} fc_j}{7},$$

where $fc_j$ is the daily frequency compliance score (1 if the patient performed the requested action and 0 if the patient did not). As illustrated, the trended frequency compliance score falls off, see group 916, when a patient action is not detected, such as at 918, until the patient has performed the requested action for a full week's time with regularity. The trended frequency compliance score will then be adjusted to a value 920 to indicate full compliance.

The fifth chart 908 in FIG. 9E illustrates a trended quality compliance score. Quality compliance may also be referred to as technique compliance. Some patient actions may be analyzed for such a compliance using the measurement value or other aspect of the requested patient action to infer or deduce a level of quality or correct technique used by the patient when executing the requested action. Similar to the trended time compliance score and the trended frequency compliance score, the trended quality compliance score may be based on prior occurrences of the patient's responsive action. In this example, the window or number of occurrences used to calculate the trended quality compliance score is illustrated as being five days. Here, the specific instructions included the instruction for the patient to measure their weight unclothed. Recognizing data outliers, such as those at 922, which are abnormally high in comparison to other data points in the first chart 900, it may be inferred or deduced that the patient improperly wore clothes while weighing in. Thus, the daily quality or technique compliance score is lower and corresponding trended quality compliance score falls off, such as at 924.

One or more of the trended time compliance score, trended frequency compliance score, or trended quality compliance score, may have an associated threshold value, such that if the trended compliance score falls below the threshold value, an alarm is issued. Threshold values are illustrated in the third, fourth, and fifth charts 904, 906, 908 as dashed lines 926, 928, 930, respectively. The threshold may be based on a statistical or probabilistic model (e.g., using a population database or previous measurements from a particular patient) or may be maintained by a user (e.g., a physician or clinician). For example, in some situations a user may want a higher or lower sensitivity to changes in different measures of compliance. Manually raising or lowering the threshold value for one or more of the trended compliance scores may allow the user to manage false positive or false negatives (e.g., specificity or sensitivity) of compliance alerts. A CFAR technique can also be used, as discussed and incorporated above.

Figure 9F:
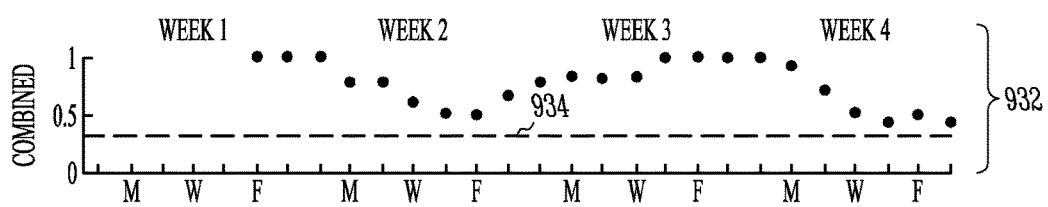

In some examples, a combined compliance score may be calculated, as illustrated in the sixth chart 932 in FIG. 9F. The combined compliance score may be a weighted function of one or more of the trended time compliance score, the trended frequency compliance score, or the trended quality compliance score. In the example illustrated, the combined compliance score is a weighted linear function of the trended time compliance score, the trended frequency compliance score, and the trended quality compliance score, each with equal weights. In an example, the combined compliance score may also be trended with respect to time. A threshold value may also be provided (illustrated as dashed line 934), such that if the combined compliance score is calculated to be less than the threshold value, an alarm is issued.

As an extension of the example illustrated in FIGS. 9A-9F, two or more requested patient actions may be recorded and analyzed. The combined compliance score, as shown in the sixth chart 932, may be a function of one or more of the time, frequency, or quality compliance scores from each of the two or more requested patient actions. One or more of the requested patient actions may be weighed differently from each other in the combined compliance score. In addition, each element of the combined compliance score (e.g., time, frequency, or quality) may also have an associated weight, which may differ from one another.

Between-Patient Diagnosis

Although monitoring a patient's physiological or other health-related indications over time may provide some insight into the patient's health-related trends, analysis may be made more complete by including a between-patient diagnosis technique. Between-patient diagnosis leverages previously recorded and documented patient data for the benefit of a current patient. By comparing the current patient to a group of similarly situated patients, probabilistic determinations may be made. For example, based on comparisons to a reference group or control group of patients, a particular patient may be said to be more similar or less similar to the reference group. As another example, using one or more other comparisons to the reference group, the particular patient may be probabilistically deemed more or less likely to experience a health event in a given amount of time (e.g., a specified "prediction time interval"), relative to the reference group. Using one or more such probabilistic measurements, a physician may change diagnosis or adjust or adapt therapy to increase the quality of life of the particular patient. For example, a physician may increase the number of follow up visits or shorten the length of time between successive follow up visits, tune one or more thresholds on one or more alert methods, or alter medication to be more aggressive or less aggressive.

In an example, a between-patient technique provides a population-based stratification of patients according to their risk of a health condition (e.g., heart failure decompensation) within a particular time frame (e.g., three months). For example, a given patient may be classified as "high," "medium," or "low" risk when compared to a reference patient population. The technique can include comparison of one or more heart rate variability (HRV) diagnostics of a patient with a model of one or more similar diagnostics of a reference population. The reference population may include one or more typically, multiple patients, that may be similar to the current patient, such as being prescribed with similar medical devices or associated with similar therapies. The between-patient technique results in an index value, which may indicate whether (or a degree to which) the patient is similar to the reference population.

In an example, one or more threshold values are used to categorize or bin the patient into a particular group associated with a risk level or category. For example, threshold values may be established using quartiles, deciles, quintiles, or the like. In other examples, a logarithmic, exponential, or other distribution function (e.g., a Bell curve) may be used to stratify a patient population into two or more risk categories or levels. Threshold values may be adjusted, such as periodically or recurring. Adjustments may be performed automatically or manually, in various examples. For example, when a reference patient population is changed or replaced, such as when new patients are added to an existing reference group, one or more threshold values may be modified to maintain a proper population distribution. Such an adjustment may occur when triggered by a user (e.g., a physician) who has confirmed the use of the revised patient population reference group. An adjustment to one or more threshold values may occur automatically, such as when a system detects the availability or use of a revised patient population reference group.

While examples illustrating the use of HRV diagnostic values are described, other physiological, psychological, or other patient indications may be used to compare a particular patient with a reference group. For example, heart rate (HR), physical activity, blood pressure, heart sounds, intracardiac or thoracic or other impedance, or other metrics may be used for categorization or comparison.

Constructing an appropriate reference group may impact the accuracy or value of any predictive calculations based on comparisons between a patient and the reference group. As such, the reference group may be selected based on one or more similarities with the patient in question. Similar patients may include:

patients who participated in the same controlled study;
  patients who are managed by the same or similar health provider, such as the same implant provider or the same therapy provider;
  patients who are viewed as stable (e.g., did not die in a particular time, did not decompensate within a particular time, are compliant in their medication or other prescriptions, report a high quality of life, or have not used the health care system in a particular time period);
  patients with similar age, gender, ethnicity, geography, clinic, left ventricular ejection fraction (LVEF), New York Heart Association (NYHA) heart failure classification, HF etiology, body mass index (BMI), blood pressure, Six-minute walk test (6 MW), quality of life (QoL);
  patients who have survived for a particular time frame (e.g., 5 years after implant or 6 months after change of therapy), patients who have not decompensated in a particular time frame (e.g., in the last 9 months);
  patients using the same or similar medication;
  patients with one or more similar co-morbidities or arrhythmia history;
  patients with a similar device implant or device implant history.

This list of similarity characteristics is not meant to be exhaustive or complete, but merely illustrative of examples of some characteristics that may be used as parameters to group or associate patients into a reference group.

Reference group patients may be selected from public or private databases. For example, patients may be selected from a database associated with a remote patient management system, such as LATITUDE® as provided by Boston Scientific Corporation's Cardiac Rhythm Management (CRM) group of St. Paul, Minn. In addition, reference groups may be static or dynamic. Static reference groups may be comprised of patients having records that existed in a database or system at the time the current patient enrolled or entered the database or system. Thus, static reference groups may represent a snapshot of patients who existed in the system at a particular time, such as at the time of enrollment of a new patient. Static reference groups may not be updated. For example, for a particular diagnostic technique, a snapshot static reference group of patients is used to satisfy assumptions made in the analysis of the particular diagnostic technique. Changes in the static reference group may invalidate the results of such a strict diagnostic technique.

Dynamic reference groups may include dynamically updated static reference groups or true dynamic reference groups. Dynamically updated static reference groups may be updated recurrently or periodically, such as weekly, monthly, seasonally, or annually. Such an update may create a new static reference group, to be used for a period of time. Dynamically updated static reference groups may also be updated at a triggering event. Examples of triggering events include an interrogation of a current patient's implantable device, an implantation of a new patient device, the introduction of a new patient device (e.g., a release of a new model, firmware, software, or other component of a patient device), the introduction of a new drug, or when a new revision of the reference group is approved by an authority, such as the Food and Drug Administration (FDA). Additional examples of triggering events include a detected change in a patient's health condition, a change of a standard of care, a change in a population statistic (e.g., lifestyle, eating habit, education, birth rate, death rate, or habits), or the like. Triggering events may also include one or more user commands to update a reference group. The user commands may include one or more parameters, such as patient age; gender; comorbidity; implant type; or other physiological, environmental, cultural, or patient-related data. In an example, the parameters act as a filter that defines a patient subpopulation, which is used as a dynamically updated patient reference group. In various examples, the parameters may be combined using logical conjunction, disjunction, or both.

A true dynamic reference group typically includes a patient reference group that modifies its contents automatically, such as in near real-time. For example, a true dynamic reference group may be defined using one or more parameters, such as those described above, to characterize and select a subpopulation of patients. When a patient experiences a change in a physiological, environmental, or other patient-related characteristic, the patient may automatically be added to or removed from the true dynamic reference group. In effect, in an example, a true dynamic reference group may be considered a dynamically updated static reference group that is updated when the reference group statistic (e.g., distribution) is requested or accessed. In another example, a true dynamic reference group may be viewed as a dynamically updated static reference group that is triggered to update at a small increment in time, such as every second, to make the reference group appear as a nearly real-time, dynamic view of a patient subpopulation.

Figure 10:
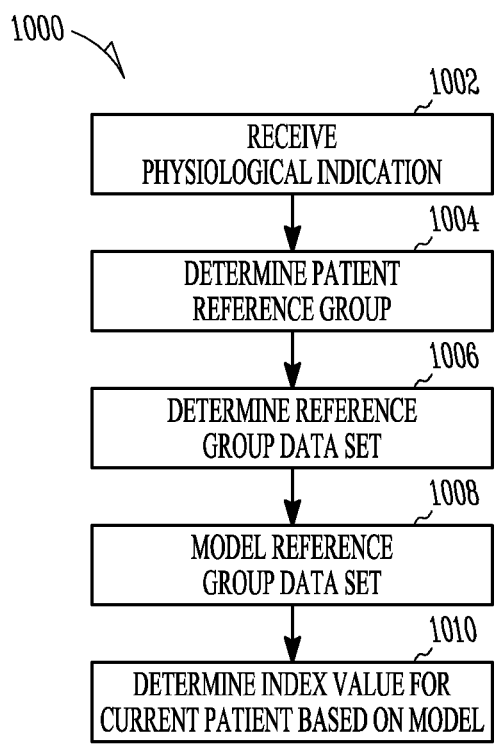
FIG. 10 illustrates an example of a method of deriving a probabilistic index based on a particular patient compared to a patient population.

FIG. 10 illustrates an example of a method 1000 of deriving a probabilistic index based on a particular patient compared to a patient population. At 1002, one or more physiological indications are received. Examples of physiological indications include sensed cardiac signals, physical activity level, and SDANN or Footprint % indices. Footprint % indices may include a measurement of an area under a 2-D histogram of heart rate variability of a patient. Physiological indications may be detected or provided by implanted or external patient monitoring devices. For example, an implanted cardiac rhythm management device may include electronics, memory, or other components to detect or store heart rate intervals, implantable electrograms, electrogram templates for tachyarrhythmia detection or rhythm discrimination, pressure (e.g., intracardiac or systemic pressure), oxygen saturation, physical activity, heart rate variability, heart sounds, thoracic or intracardiac or other impedance, respiration, intrinsic depolarization amplitude, heart rate, data related to tachyarrhythmia episodes, hemodynamic stability, therapy history, autonomic balance, heart rate variability trends or templates, or trends, templates, or abstractions derived from sensed physiological data.

At 1004, a patient reference group is determined or otherwise mapped to the current patient. As described above, the patient reference group may comprise patients from a pool of patients that share one or more similarities with the current patient. Increasing the number of similarities shared between the reference group and the current patient may increase the quality or accuracy of predictive calculations. Determining a relevant reference group may include considering one or more other factors, such as age, gender, medication, medical history, or the like, such as those described above.

At 1006, a reference group dataset is determined. In an example, the reference group dataset includes patient data of patients in the reference group, where the patient data is substantially similar to the physiological indications received at 1002. For example, if at 1002, a patient's physical activity levels are being monitored and reported by an internal or external patient device, then at 1006, patient data associated with physical activity level from the patient reference group is selected as the reference group dataset.

At 1008, a model of the reference group dataset is determined. In an example, the model is a probabilistic model and calculated using a probability function. In a further example, the probability function includes a cumulative distribution function (CDF). For example, the model may include a series of 1-dimensional (1D) empirical cumulative distribution functions of the reference group's weekly-averaged activity, SDANN, and Footprint % values. As another example, the CDF may include a single joint multivariable CDF with either a diagonal or full covariance matrix. In another example, the probability function includes a probability distribution function (PDF). In an example, a probabilistic model may include a series of 1-D probability distribution functions (PDF), where a particular PDF models a distinct parameter. In another example, the model may include a single joint multi-dimensional PDF, where each dimension models a distinct parameter. For example, a PDF may include a joint multivariable PDF with either a diagonal or full covariance and may be estimated over the reference group patients' weekly-averaged activity, SDANN, and Footprint % values. Other physiological parameters may be used in the modeling and comparison, such as average heart rate, maximum heart rate, minimum heart rate, respiration rate, amplitude of S3 heart sound, or pulmonary artery pressure.

At 1010, the current patient's received physiological value can be used to determine an index value based on the model of the reference group dataset. The index value may be calculated periodically or recurrently, such as daily, weekly, or monthly, such as by using average values for the periodic or recurrent time interval. In an example, 1-dimensional CDFs can be used as "look up tables" to determine what percentage of reference group patients had physical activity levels less than or equal to the current patient's physical activity level. A similar process may be used with SDANN and Footprint % values. For each percentile, values near 0.5 can indicate that the patient is in the $50^{th}$ percentile of the reference group (e.g., the patient is similar to the reference group), while values near 0 or 1 indicate that the patient is dissimilar to the reference group. The individual indices may be combined into a composite index, such as, for example, by multiplying, adding, or otherwise mathematically combining the individual indices.

In another example, a probability distribution function (PDF) can be used to model the reference group dataset. For example, a PDF may be constructed using the reference patients' activity, SDANN, and Footprint % values. The current patient's physiological values can be compared to an estimated PDF to determine the patient's index value. The index value may include the negative log-likelihood that the current patient's set of activity, SDANN, and Footprint % values belong to the PDF. In certain examples, the index value may also be the area under the PDF enclosed by (or outside of) an equiprobable contour that represents the probability that the current patient's set of values belong to the estimated PDF. In either case, a low (or high) index value indicates how similar (or different from) the current patient is compared to the reference group.

The index value may be advantageous to provide easier comparison between patients, provide a reference value that is easy to interpret, provide easier identification of any outlier values, or provide more insight into one or more correlations between patient physiological indications and probabilistic diagnoses. In some examples, the index value may indicate how likely a patient is to enter or recover from a disease state in a particular amount of time. As an illustration, the index value may be interpreted to indicate the likelihood of a patient to experience heart failure decompensation in the next six months, such as relative to other patients in the patient reference group. For example, Hazard ratios or Cox Proportional Models may be used to determine such a likelihood. In other examples, the index may be used to indicate how likely a patient is to experience a change in health, such as an increase or decrease in quality of life, or a likelihood of death in a particular timeframe.

Figure 11A:
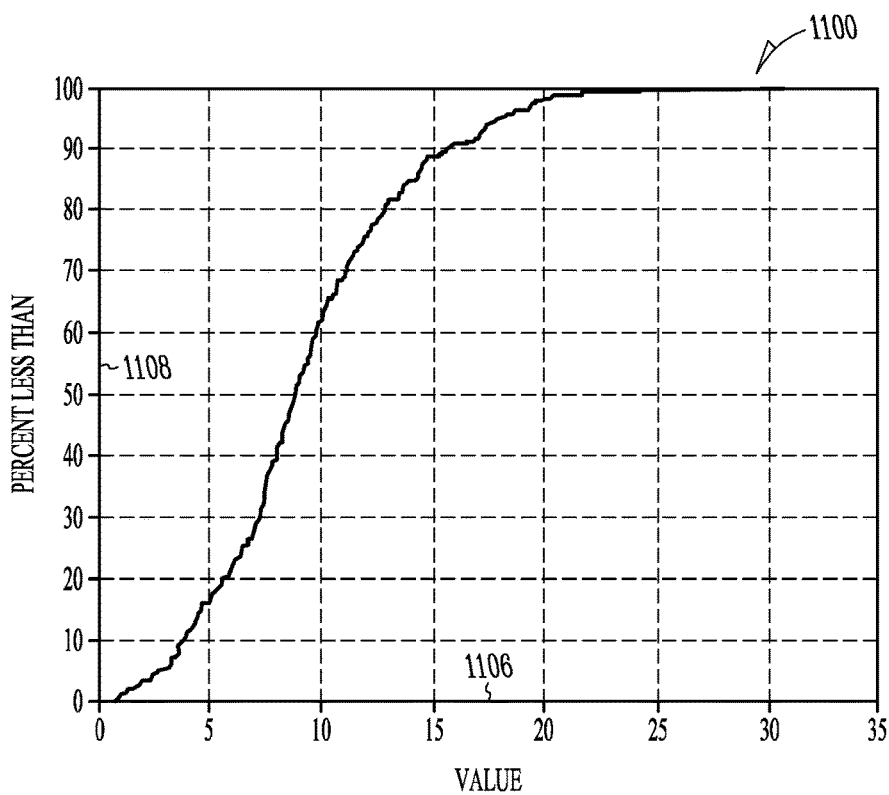
FIGS. 11A-C illustrate examples of a physical activity cumulative distribution function (CDF) chart, an SDANN CDF chart, and a Footprint % CDF chart.
Figure 11B:
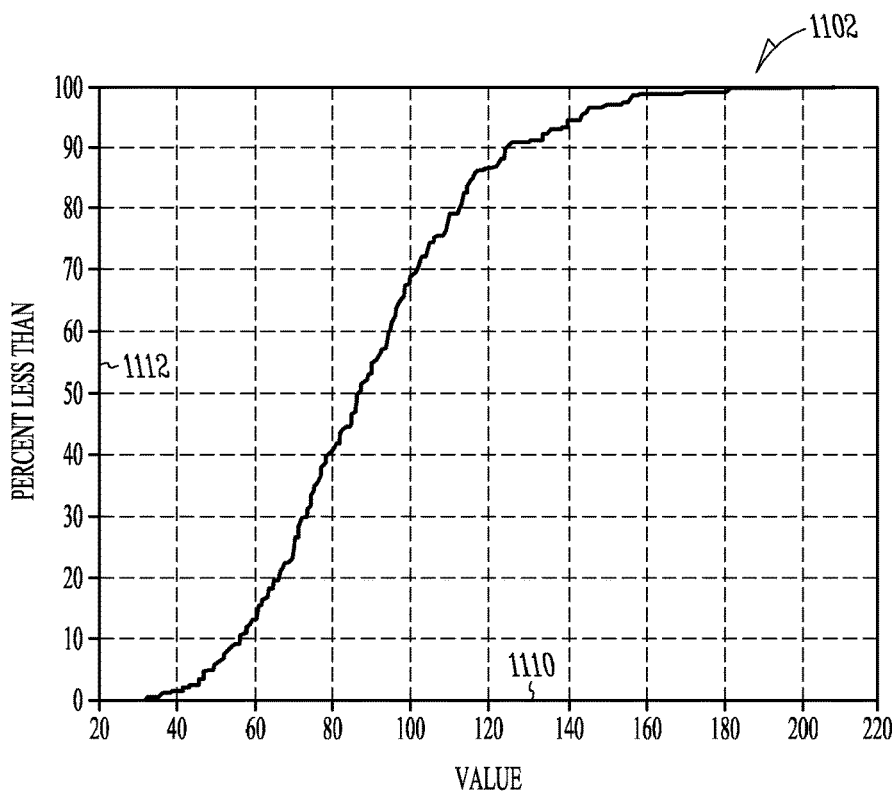
Figure 11C:
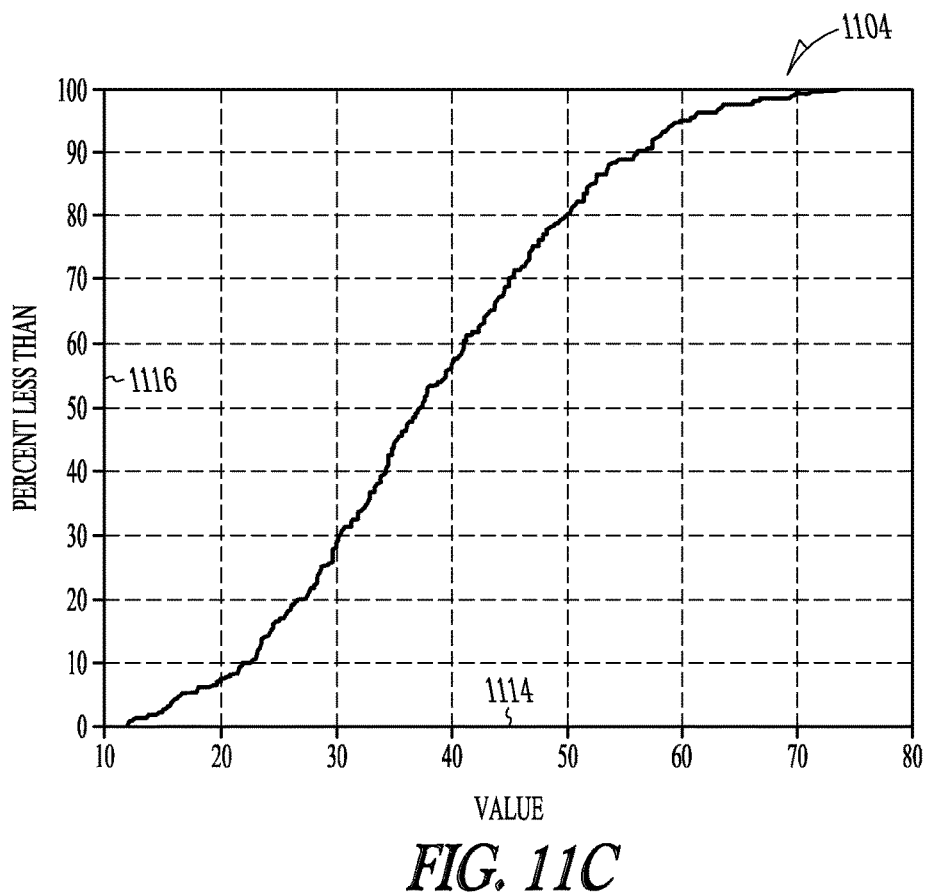

FIGS. 11A-11C illustrate examples of a physical activity cumulative distribution function (CDF) chart 1100 in FIG. 11A, an SDANN CDF chart 1102 in FIG. 11B, and a Footprint % CDF chart 1104 in FIG. 11C. In FIG. 11A, the activity CDF chart 1100 includes an activity value 1106 along the x-axis and an activity index 1108 along the y-axis. The activity value 1106, in an example, represents the percentage of time a patient is considered active using a threshold, which may be based on heart rate, blood pressure, accelerometer, or one or more other indications of physical activity. The activity index 1108 represents the percentile of a particular patient with a particular activity value 1106. For example, a patient with an activity value 1106 of 10 has a corresponding activity index 1108 of approximately 0.62, which indicates that the patient is in the $62^{nd}$ percentile of active patients, e.g., the patient is more active than 62% of the patients represented.

Similarly, in FIG. 11B, the SDANN CDF 1102 includes a standard deviation value along the x-axis 1110 and a SDANN index 1112 along the y-axis. In an example, the SDANN index 1112 represents the percentage of patients that have a SDANN value equal to or less than the corresponding standard deviation value 1110.

In FIG. 11C, the Footprint % CDF 1104 maps a footprint percentage 1114 against a footprint index 1116. In an example, the footprint index 1116 represents a percentile of patients who have a footprint percentage value equal to or less than the corresponding footprint percentage 1114.

Figure 12:
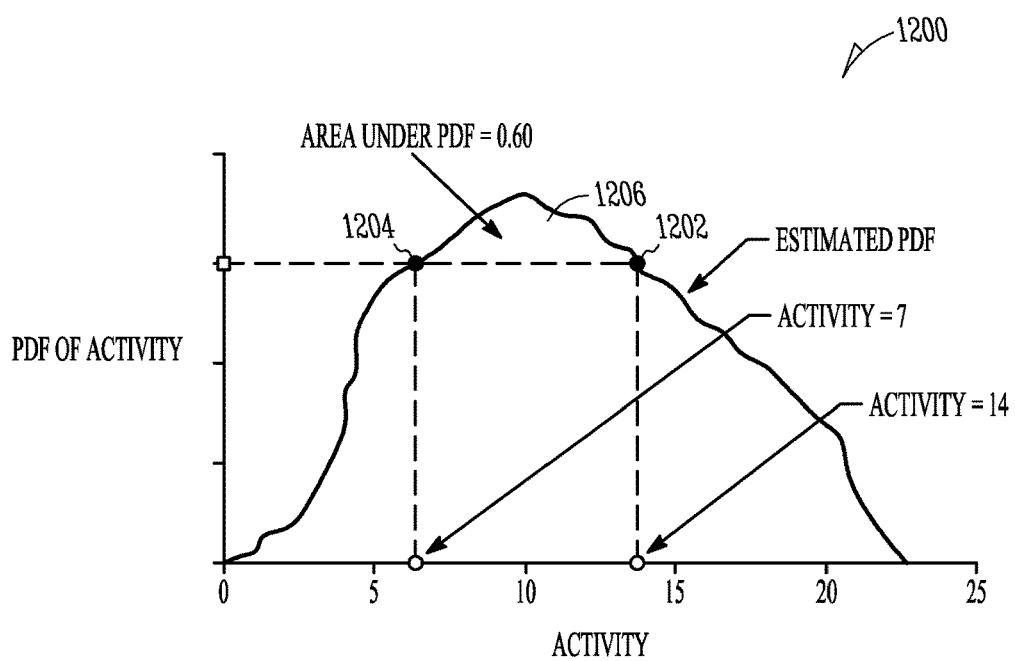
FIG. 12 is an example of a probability distribution function chart that illustrates reference group patients' physical activity levels.

FIG. 12 is an example of a probability distribution function chart 1200 that illustrates reference group patients' physical activity levels. The chart 1200 includes activity values on the x-axis and a percentage of patients who have the corresponding activity on the y-axis. To determine an activity index for a particular patient, the area under the probability distribution function (PDF) curve is calculated. In the example illustrated, by using equations that describe the probability distribution function chart 1200, it can be calculated that a patient with an activity level of 14 corresponds to a point 1202 on the curve. The 1-D activity PDF shown in FIG. 12 identifies a pair of points with equivalent probability density that defines an interval of integration. By analogy, a 2-D density would yield sets of points with equivalent probability densities or contours that would define areas of integration. In the example illustrated in FIG. 12, point 1202 and point 1204 share a common probability density. Using the two points 1202, 1204, an area 1206 under the PDF is defined. In an example, the activity index is equal to the area 1206 under the PDF. Using the calculated activity index may provide advantages, including easier comparison between several patients or easier communication of a patient status to the patient or other medical professionals.

Inter-Relationship Between within-Patient Diagnosis and Between-Patient Diagnosis A between-patient analysis may provide a more long-term indication of a patient's risk compared to a population. In contrast, a within-patient analysis may provide a more short-term indication of acute changes in a patient's health. Thus, it may be advantageous to use one analysis to tune performance of another analysis. For example, a between-patient analysis that includes a large number of patients in the population may provide a sufficient confidence that a particular patient is high or low risk for the occurrence of a particular physiological condition. If the patient is considered high-risk, then one or more parameters of a within-patient analysis may be modified. For example, sampling timing intervals may be shortened to detect acute changes quicker, threshold values may be revised, or a probability distribution model may be selected based on the type or severity of the population-based risk. In contrast, if the patient is considered low-risk or lower risk, then a within-patient analysis may not be considered necessary. Alternatively, the within-patient analysis in such a situation may be revised to less be invasive or have reduced sensitivity and increased specificity (e.g., to reduce false alarms). Such a system may allow physicians to stratify patients according to their long-term risk using the between-patient technique and keep a closer watch for acute changes in patients with higher risk using the within-patient technique.

Figure 13:
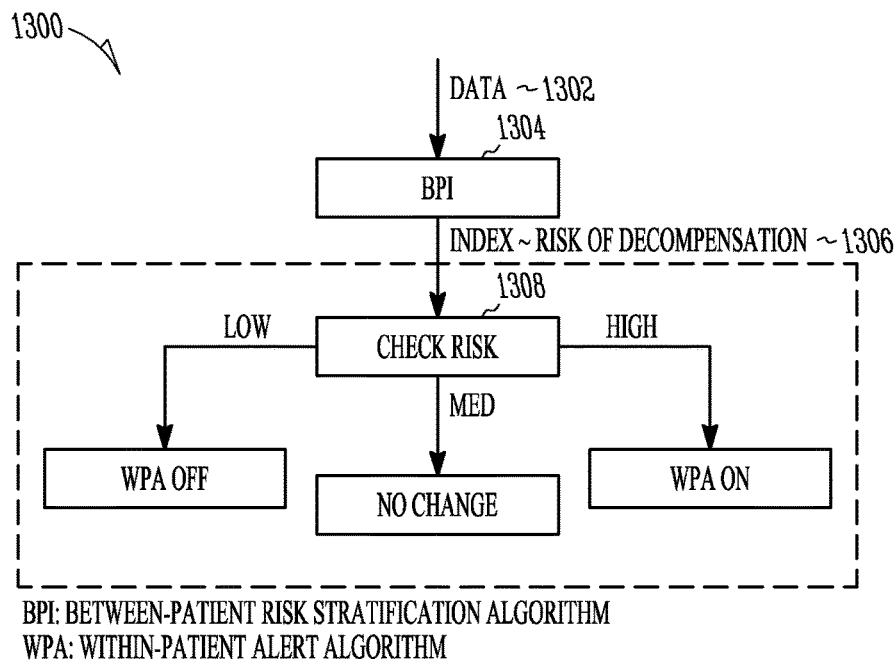
FIGS. 13 and 14 are diagrams illustrating examples of control and data flow between patient analysis processes.

In an example, a within-patient decompensation detection technique may be enabled or disabled when a low or high index value is returned from a between-patient risk stratification technique. FIG. 13 is a diagram 1300 illustrating an example of control and data flow between patient analysis processes. Sensor data 1302 is received and analyzed by a between-patient diagnostic technique 1304, such as one described above. The between-patient diagnostic technique 1304 outputs an index 1306 indicative of a risk or likelihood of a patient experiencing a disease or other health concern similar to that of the population used in the between-patient diagnostic technique 1304. A control module 1308 receives the index 1306 and compares it to a risk threshold. In an example, the risk comparison results in a tri-state output, such as "low," "medium," and "high" risk in comparison to a threshold value or a range of threshold values. When the index 1306 is associated with a low risk, then a corresponding within-patient alert (WPA) technique is disabled 1308. When the index 1306 is associated with a medium risk, then no change is made—if the WPA technique was enabled, then it remains enabled, and if the WPA technique was disabled, then it remains disabled. When the index 1306 is associated with a high risk, then the WPA technique is enabled. In an example, the WPA technique is enabled or disabled automatically. In another example, a user (e.g., an attending physician) may be notified of the suggested change in WPA state and may then manually or semi-automatically enable or disable the WPA technique.

Example: After a hospitalization, cardiac diagnostics may stabilize due to the effect of a drug therapy resulting in a lower index value (result of a between-patient diagnostic technique). In light of the lower index value, the within-patient technique may no longer be considered necessary. Thus, the within-patient technique may be disabled automatically or manually to reduce false alarms that may result from acute changes in patient data.

Example: After an implant procedure, if the index value from a between-patient technique is high enough (e.g., greater than a threshold value), it may imply that the patient is sufficiently different from a reference group comprising stable CRT-D patients that a physician may choose to maintain a closer watch on the patient. To do so, the physician may enable within-patient technique to alert the physician of acute changes in diagnostic parameters.

In an example, one or more parameters of a within-patient technique may be enabled, disabled, or modified based on the result of a between-patient technique. For example, an acute detection threshold may be adjusted based on one or more population-based risk assessments. As another example, a measurement probability distribution function (PDF) model may be selected based on the population-based result (e.g., using a Gaussian or lognormal PDF model).

Figure 14:
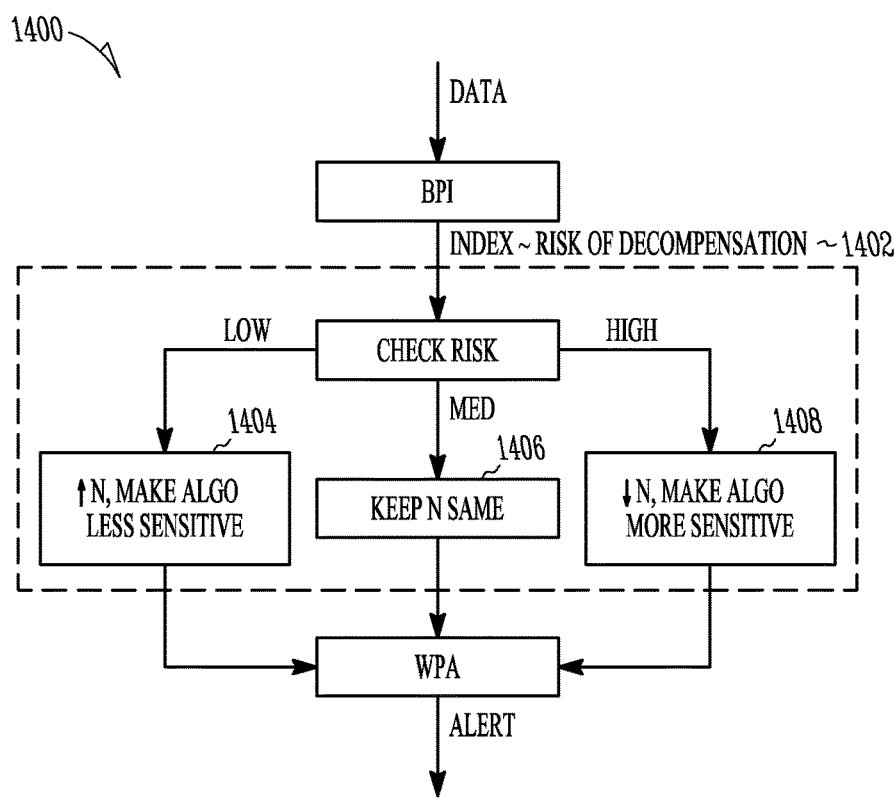

FIG. 14 is a diagram 1400 illustrating an example of control and data flow between patient analysis processes. Similar to the system described in FIG. 13, based on an index value 1402, risk can be assessed with a tri-state output. In this illustration, when the risk is considered low, then one or more parameters in the within-patient technique are modified to make the technique more specific and less sensitive 1404. When the risk is considered high, then the technique is made more sensitive and less specific by adjusting the one or more parameters 1406. Finally, when the risk is considered medium, then the one or more parameters are maintained at their current values 1408. Parameters may include weights in a weighted function (weighting factors), models used for patient comparison, one or more threshold values, or the like. Parameters may also include variables that control conditional states (e.g., control flow), sample resolution (timing), frequency of assessment, pattern of assessment (e.g., time of day, sequencing of multiple assessments), or the like. For example, one or more parameters may be automatically determined or provided by a user (e.g., a physician or clinician) to indicate which of one or more analysis processes are evaluated and in which order after a preceding analysis is completed. Controlling the selection and arrangement of the analysis processing may be advantageous to refining the analytical result or reducing processing errors (e.g., false positive or false negative indications).

By automatically or manually adjusting the parameters of the within-patient technique, false alerts may be reduced or minimized, which may allow patients to be managed more efficiently. In an example, some parameters are adjusted automatically. In another example, one or more proposed changes to parameters are presented to a user, for example, an attending physician, who then may either permit or deny changes to the parameters.

Example: If a between-patient stratifier technique indicates that SDANN has a higher sensitivity for a particular patient compared to minimum heart rate (HRMin), then a within-patient technique may be modified to assign a higher weight to an SDANN parameter in a weighted function.

In certain examples, one or more performance parameters of a first technique, such as a between-patient stratifier, may be adjusted to affect the false positives, false negatives, specificity, sensitivity, positive predictive value, negative predictive value, number of false positives per year of a second technique, such as a within-patient technique.

As described above, sensitivity generally refers to the ability of the detection scheme to effectively detect a particular result. Sensitivity can be expressed with the formula: sensitivity=(true positives)/(true positives+false negatives). Thus, a higher sensitivity generally indicates that an analysis correctly characterizes more true positives or eliminates false negatives.

Specificity generally refers to the ability of the detection scheme to avoid improper classifications. Specificity can be expressed with the function: specificity=(true negatives)/(true negatives+false positives). Thus, a higher specificity generally reflects more accurate classification of true negatives or reduction of false positives.

Positive predictive value (PPV) generally refers to the ability of the detection scheme to accurately produce correct positive results. PPV can be expressed with the function: PPV=(true positive)/(true positives+false positives). Thus, PPV exhibits a ratio of correct positive indications.

Negative predictive value (NPV) generally refers to the ability of the detection scheme to accurately produce correct negative results. NPV can be expressed with the function: NPV=(true negatives)/(true negatives+false negatives). Thus, NPV exhibits a ratio of correct negative indications.

False positives (FP) per year is a ratio of false positive indications over one or more years. False positives per year can be expressed with the function: FP/yr=(FP in one or more years)/(number of years).

In an example, a within-patient technique may be used to influence a between-patient technique. For example, the between-patient technique may be enabled, disabled, or have one or more parameters modified or enabled based on the results of the within-patient technique.

Figure 15:
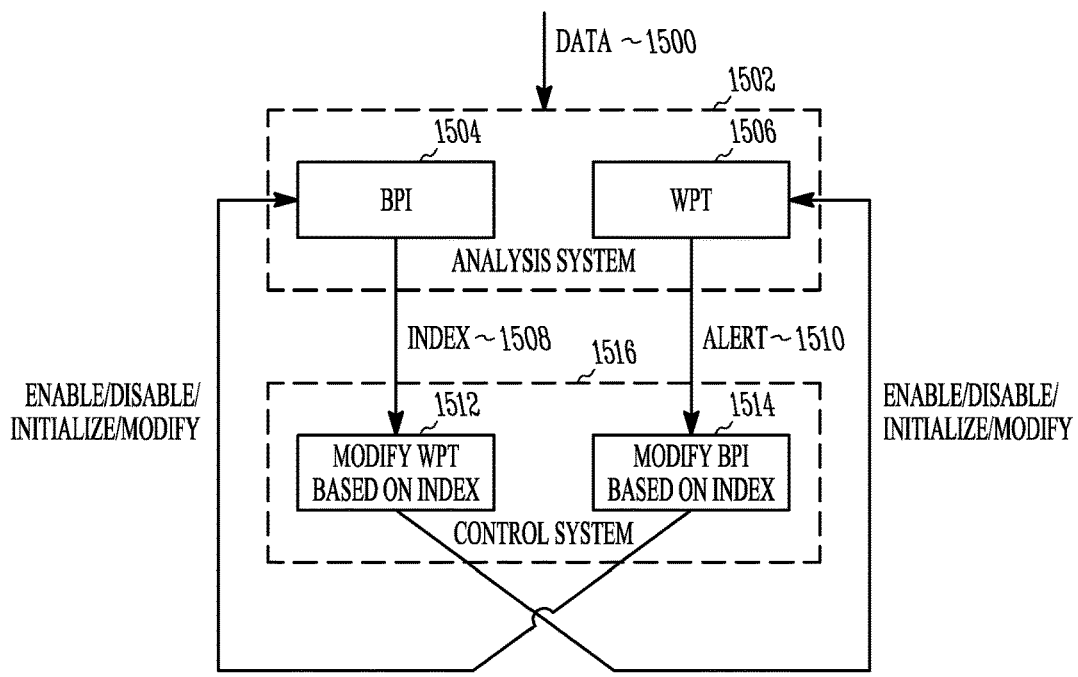
FIG. 15 illustrates a cross-feedback configuration of patient analysis processes.

FIG. 15 illustrates a cross-feedback configuration of patient analysis processes. Patient data 1500 is received at an analysis system 1502. In an example, the analysis system includes a remote patient management system, such as LATITUDE®. A between-patient index technique 1504 or a within-patient technique 1506 may use the received patient data 1500 to calculate an index 1508 or an alert 1510, respectively. In an example, the index 1508 indicates how similar a patient is to a patient population (e.g., reference group). In an example, the alert 1510 indicates an acute change in patient physiological parameters. The index 1508 and the alert 1510 are received at a control system 1516. In an example, the control system 1516 is part of the same system as the analysis system 1502, e.g., LATITUDE®. In other examples, the control system 1516 and the analysis system 1502 are in separate devices. For example, the analysis system 1502 may be located in a programmer, while the control system 1516 may be located at a centralized patient management server. A first module 1512 in the control system 1516 determines whether to modify the within-patient technique 1506 based on the calculated index 1508. A second module 1514 in the control system 1516 determines whether to modify the between-patient index technique 1504 based on the alert 1510. In either case, examples of the modifications may include enabling, disabling, initializing, or modifying one or more parameters of the corresponding technique.

In another example, three or more diagnostic techniques are configured to interact with each other. For example, a first between-patient diagnostic technique may be configured to focus on physical activity levels, a second between-patient index may be configured to focus on heart rate variability, and a third within-patient diagnostic technique may also be available. The results of the within-patient diagnostic technique (third technique) may affect one or both of the between-patient techniques (first and second). In other examples, two of the techniques may be configured to affect the third. In other examples, one technique may be used to determine which subsequent technique is used or in what order subsequent techniques are performed. In such a configuration, the collection of techniques may be viewed as a state machine. Creating a matrix or "web" of one or more permutations or combinations of between-patient or within-patient diagnostic techniques may provide higher efficiency in diagnosis or fewer false positive or false negative indications.

Physician Feedback

In some situations, diagnostic techniques, such as those described herein, may result in false positive or false negative indications. For example, false indications may occur when a technique is first initialized to a general state before the technique has been revised or tuned for a particular patient. To reduce the number of false indications and improve accuracy, it may be advantageous to allow a medical professional to monitor and control such diagnostic techniques.

Figure 16:
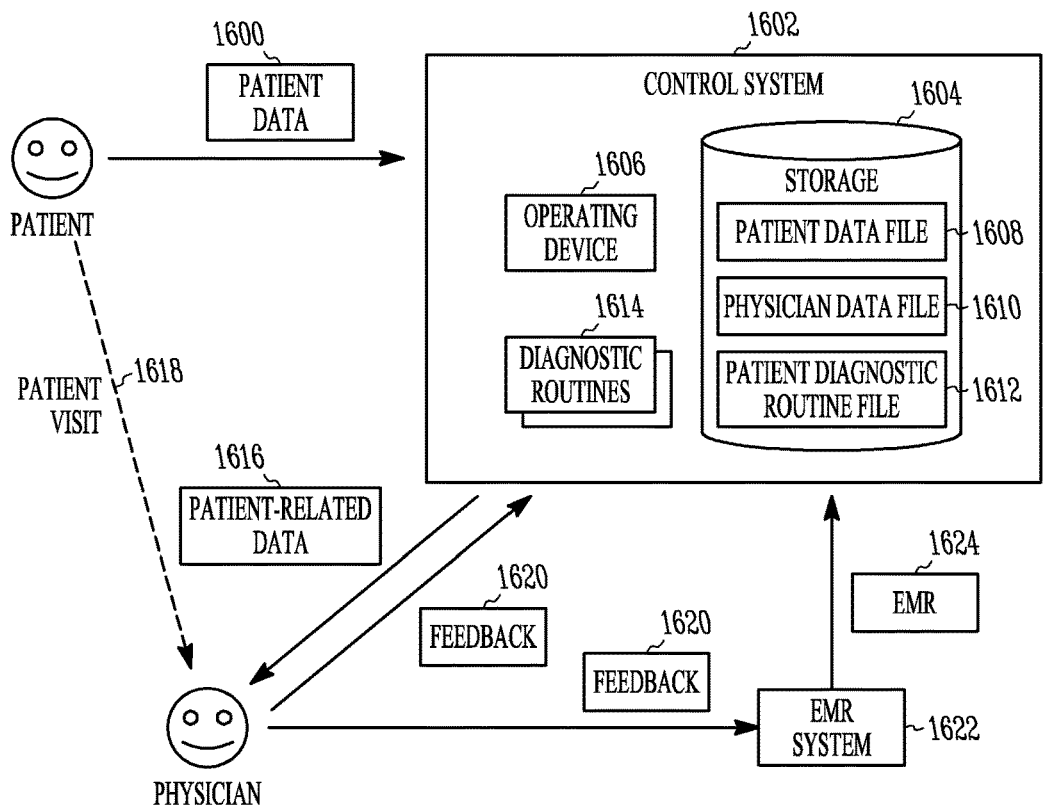
FIG. 16 is a dataflow diagram illustrating an example of a physician feedback process.

FIG. 16 is a dataflow diagram illustrating an example of a physician feedback process. Patient data 1600 is communicated to a control system 1602. Patient data 1600 may include physiological data, environmental data, or subjective patient responses, in various examples. In an example, the control system 1602 includes some or all of the components described in 108 (FIG. 1). In the example illustrated in FIG. 16, the control system includes a storage device 1604 and an operating device 1606. The storage device 1604 may be configured as a database, a file structure, or other storage means. The storage device 1604 typically includes a patient data file 1608, a physician data file 1610, and patient diagnostic routine file 1612.

The patient data file 1608 may include historical physiological data such as in raw or summarized format, historical subjective responsive patient data, one or more alerts generated from one or more patient detection techniques, trending data, extrapolated data (e.g., minimum, maximum, or median patient-related values for a particular timeframe), or other patient-related information (e.g., patient identification information, hospitalization information, historical automatic or physician diagnoses, etc.).

The physician data file 1610 may include physician notes or comments related to a particular patient, physician input (as described in further detail below), prescribed therapies, or other physician-related information.

Patient diagnostic routine file 1612 may include programmatic code or other structures that control or enable the decisional process of an automated patient evaluation. Patient diagnostic routine file 1612 may also include variables, such as threshold values, weighting factors, or other parameters used during the execution of patient diagnostic routines.

The operating device 1606 may include one or more computers or other programming devices to control the execution of patient diagnostic routines 1614. In an example, the operating device 1606 may access patient data from the patient data repository 1608, initialize one or more patient diagnostic routines 1614 using parameters stored in the patient data file 1608 or the patient diagnostic routine file 1612, execute the patient diagnostic routines 1614, and store results in the patient data file 1610 or the patient diagnostic routine file 1612.

At some time, a physician or other medical professional may access the control system 1602 and receive patient-related data 1616. Patient-related data 1616 may include physiological data, test results, summary data, patient diagnostic parameters, patient therapies, or other patient data stored in the patient data file 1608 or the patient diagnostic routine file 1612. The physician may have an opportunity to interview or examine the patient, such as during a patient visit 1618. Using the observation, interview, or other information, the physician may provide feedback 1620 to the control system 1602. In an example, the physician may provide physician input (e.g., feedback 1620) to the control system 1602 using an observation, interview, examination, or evaluation of a patient or patient-related data. Such input may be independent from a contemporaneous result generated at the control system 1602, such that the physician may not have reviewed test results or may not have been provided with test results in the patient-related data 1616. An independent evaluation of a patient, not biased by a result generated by the control system 1602, may advantageously provide a "gold standard" or truth standard, by which the control system 1602 may adapt its methods or processes to be more accurate when compared to the physician's assessment.

In some examples, a physician or clinician may provide input or feedback using a terminal, for example as illustrated at 112 (FIG. 1). In some examples, a physician or clinician may provide input to an electronic medical records system 1622. Some or all of an electronic medical record 1624 (EMR) stored at the electronic medical records system 1622 may then be imported to control system 1602. Portions or all of physician feedback 1620 may be stored in the physician data file 1610. In an example, the operating device 1606 may use physician feedback 1620 to alter or adjust the execution of one or more patient diagnostic routines 1614.

Figure 17:
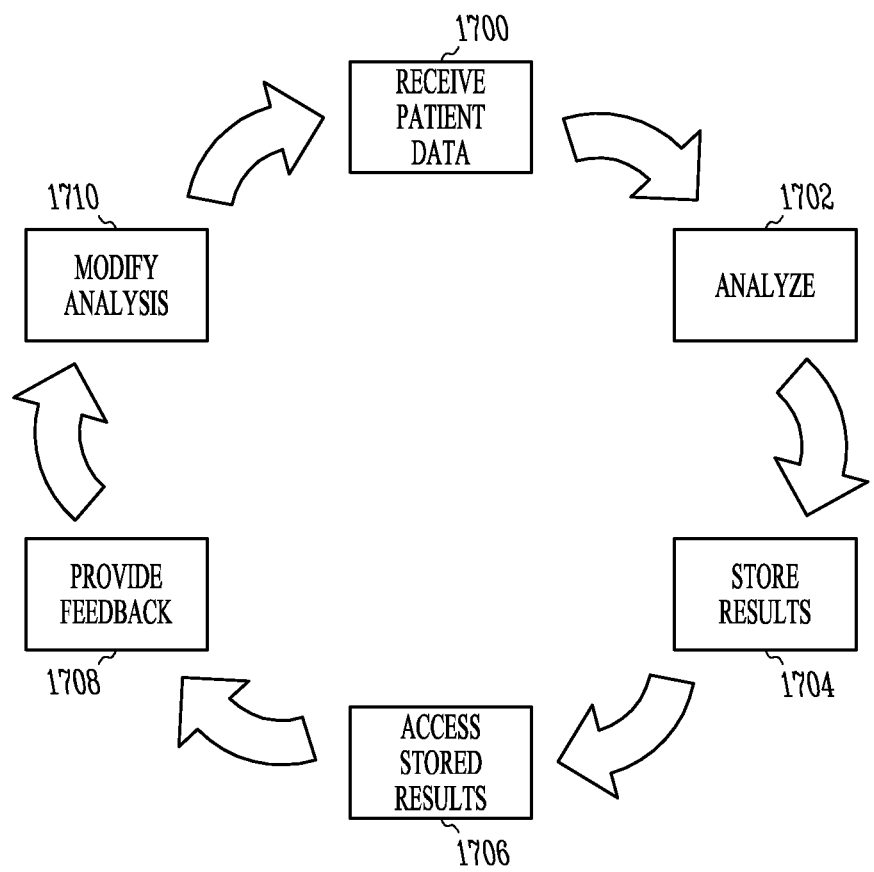
FIG. 17 illustrates an example of a feedback loop between a central system and a physician.

FIG. 17 illustrates an example of a feedback loop between a central system and a physician. At some time, patient data is received 1700. The patient data is analyzed 1702 by one or more patient diagnostic routines. Results of the analysis are stored 1704. A physician or clinician may access and review 1706 the stored results. The physician or clinician may provide feedback 1708. The feedback may be in the form of a verification (e.g., correct or incorrect result) or one or more commands (e.g., increase specificity or decrease threshold of a particular patient diagnostic routine), in various examples. The feedback may be an independent assessment of a patient in an example. In examples, the feedback message may be in the form of one or more standardized languages (e.g., eXtensible Markup Language (XML)) or in a standardized format (e.g., comma-separated file (.csv)). Using the physician or clinician's feedback, one or more parameters of the analysis are modified 1710, which may affect later execution.

Figure 18:
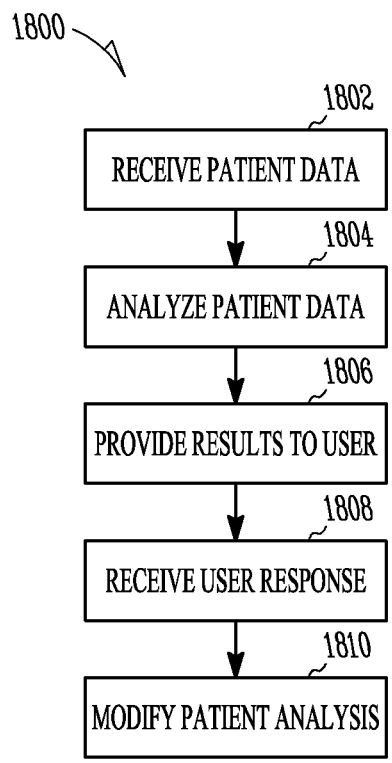
FIG. 18 is a flowchart illustrating an example of a method of using physician feedback to modify the execution of patient analysis routines.

FIG. 18 is a flowchart illustrating an example of a method 1800 of using physician feedback to modify the execution of patient analysis routines. At 1802, patient data is received. Patient data may originate from one or more sources, including sensed physiological data from one or more implanted or external monitoring devices, patient response data from an interactive or interrogatory device, or health data obtained during an office visit or other examination or interview with a medical professional. Patient data may also be retrieved or received from an external data source, such as an electronic medical records database.

At 1804, the patient data is analyzed with one or more patient diagnostic analyses, such as those described above (e.g., within-patient technique or between-patient technique). At 1806, the results of the analysis are provided to a user. In an example, the results are automatically forwarded to a user when certain conditions exist, for example, when an alert has been generated. In another example, the results are stored for later access by a user.

At 1808, a response is received from the user. The response may include a verification message in an example. The verification message may indicate that the results of the analysis were correct or incorrect based on further investigation by the user, for example. In another example, the response may include one or more user directives. The user directive may occur alone or in combination with a verification message. User directives may include increasing or decreasing an analysis' sensitivity or specificity; raising, lowering, or providing a particular value for a threshold or other parameter; or increasing, decreasing, or providing a particular value for an importance or ranking of a sensor or measurement. Further examples of user directives are described below.

At 1810, one or more aspects of patient diagnostic analyses are modified or adjusted using the response. Modifications may include enabling or disabling an analysis, increasing or decreasing one or more weights in a weighted function associated with an analysis, or modifying an alert detection technique (e.g., by raising or lowering a threshold). Other modifications may be implemented, such as choosing one predictive or discrimination technique over another or choosing which techniques to use together. For example, in the context of tachyarrhythmia discrimination and detection, a physician may decide to use a morphology-based discrimination algorithm (e.g., Rhythm ID) over an interval-based discrimination algorithm (e.g., one-button detection enhancement (OBDE)). As another example, in the context of heart failure decompensation detection or prediction, a physician may choose to blend the results of a pulmonary edema detection with an electrical dysynchrony detection.

Figure 19:
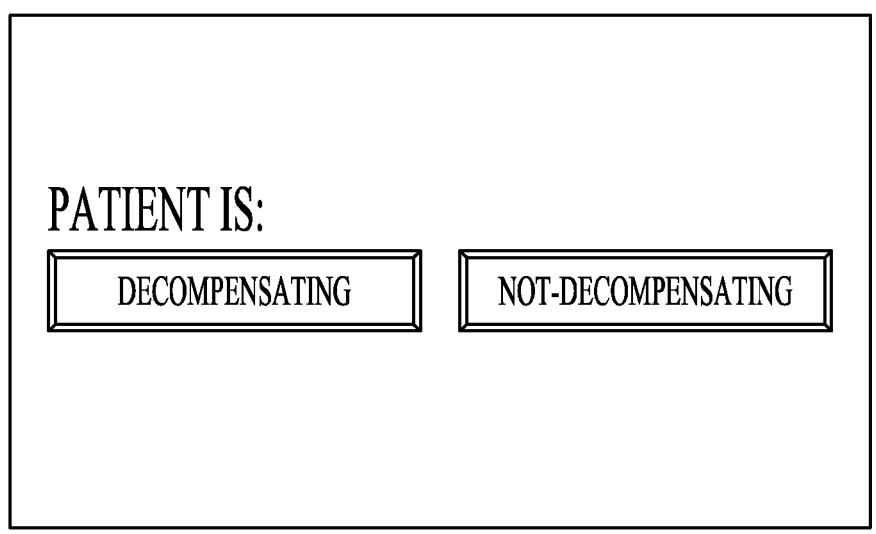
FIG. 19 is an example of a user-interface to allow a medical professional to submit input or feedback to a control system.

FIG. 19 is an example of a user-interface to allow a medical professional to submit input or feedback to a control system. In the example illustrated, a medical professional may provide an indication of whether a heart failure patient is decompensating. Such an indication is provided independent from any result calculated from the control system. For example, a physician may independently examine or interview a patient and derive a diagnosis without referring to a diagnosis generated by the control system. The indication need not be tied to a particular diagnostic analysis. For example, the physician may provide an indication that may be related to one or more within-patient diagnostic techniques and/or one or more between-patient diagnostic techniques. In various examples, the medical professional may be presented an input to provide one or more health characterizations (e.g., aspects of decompensation, arrhythmia, weight gain, blood pressure), some of which may be used by the control system (e.g., 1602 in FIG. 16) to modify a parameter or other aspect of a patient diagnostic technique, or a sensor's detection process.

Figure 20:
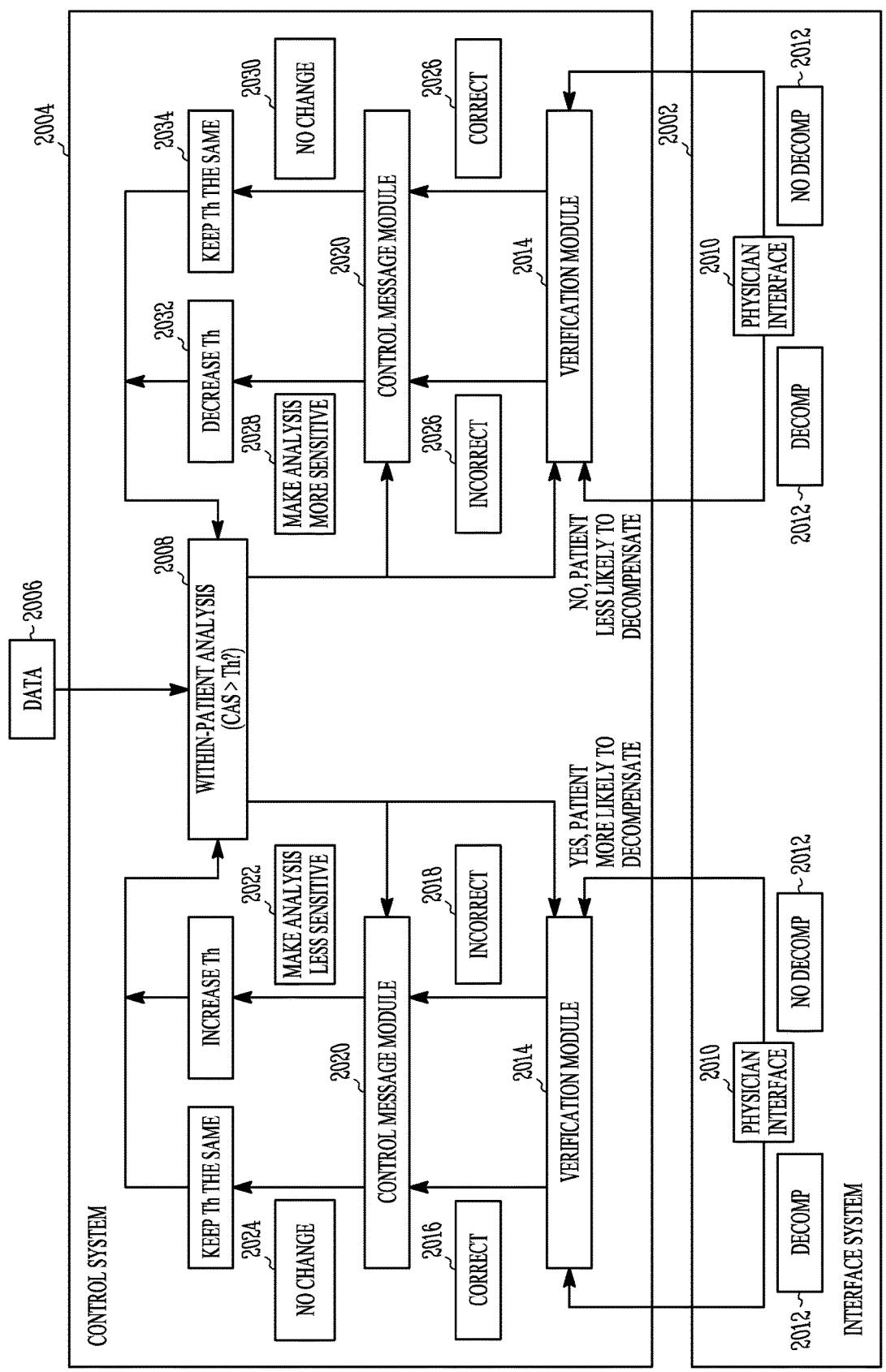
FIG. 20 is a control flow diagram illustrating an example of an interaction between a user-interface system and a control system in accordance with the user-interface illustrated in FIG. 19.

FIG. 20 is a control flow diagram illustrating an example of an interaction between a user-interface system 2002 and a control system 2004 in accordance with the user-interface illustrated in FIG. 19. In an example, the user-interface system 2002 is incorporated into a user terminal, such as illustrated in FIG. 1 at 112. In an example, the control system 2004 is incorporated into a remote server system, such as 108 in FIG. 1. In the example illustrated in FIG. 20, data 2006 is received by the control system 2004 and analyzed by a within-patient analysis 2008, such as an analysis described herein. A composite alert score is evaluated and compared to a threshold value (Th). If the composite alert score is greater than the threshold (Th), then the status is presented to a physician interface 2010, such as for display. In examples, the physician interface 2010 may include a computer terminal, an electronic medical records system, or other input mechanism. A physician may make an independent determination of the patient's status, for example during an office visit or during a telephonic patient interview. The physician may then provide the independent determination using the interface, such as an interface illustrated in FIG. 19. The independent determination may be performed asynchronously with contemporaneous evaluations performed by the control system 2004 or other systems, such that, for example, the independent determination may occur before, during, or after a particular within-patient analysis 2008 has been evaluated. The independent evaluation may rely on, at least in part, data similar to that received by the control system 2004, such as data 2006, or may use independently obtained data, such as data obtained during a patient examination, or may use a combination of data sources. Whatever the source of data, the independent evaluation is typically made without reference to automatically determined results, such as results of within-patient analysis 2008. In an example, the independent evaluation is stored at an electronic medical records store and later communicated to the control system 2004 in the form of an assessment message.

The independent determination may take the form of an assessment message 2012. One or more assessment messages 2012 are communicated to a verification module 2014 in the control system 2004. In various examples, the assessment message 2012 may be formatted using a standardized interface language, such as XML, or in a standard file format, such as comma-separated values (csv) or a tab delimited format. The verification module 2014 also has access or is provided one or more aspects of the analysis 2008, such as current threshold values, current sensors used, or current CAS value. The verification module 2014 may include one or more programmatic modules, such as software programs, to compare the physician's assessment message 2012 with the output of the analysis 2008. For example, when the physician indicates that the patient is decompensating, if the results of the analysis 2008 indicate that the patient is more likely to decompensate, then the verification module 2014 generates a verification message 2016 indicating that the result of the analysis was correct. In various examples, the verification message 2016 may be formatted using a standardized interface language, such as XML, or in a standard file format, such as comma-separated values (csv) or a tab delimited format. However, if the physician indicates that the patient is not decompensating, then the verification module 2014 generates a verification message 2018 indicating that the result of the analysis was incorrect.

The verification message 2016, 2018 is received by a control message module 2020. The control message module 2020 also has access to or is provided with one or more aspects of the analysis 2008. The control message module 2020 may include one or more programmatic units, such as software, hardware, or a combination of both, containing instructions to determine what type of modification if any, is communicated to the analysis 2008. For example, when the within-patient analysis 2008 indicated an alert state and the verification message 2018 indicates that the result was incorrect, then in an example, the control message module 2020 generates a control message 2022 to reduce the sensitivity of the analysis and the control system 2004 may then increase the threshold value 2014 to make the analysis 2008 more specific in later evaluations. By increasing the threshold value and making the analysis more specific, the physician may affect the analysis to reduce false positives in later evaluations. In certain examples, the control message module 2020 may have access to or be provided with one or more parameters that influence which control message is generated in a particular situation. For example, if an analysis is incorrect and the threshold value has been increased several times, then the control message module 2020 may generate a control message 2024 indicating to maintain the current threshold value.

In a similar fashion, if the composite alert score does not exceed the threshold, then that result may also be presented to the physician interface 2010. The physician may make a similar independent evaluation of the patient's status and submit an assessment message 2012 to the verification module 2014 in the control system 2004. The verification module 2014 then compares the physician's independent evaluation, contained in the assessment message 2012 with one or more aspects of the result of the analysis and generates a verification message 2026. The verification message 2026 is then communicated to the control message module 2020 and a control message 2028, 2030 is generated. The control system 2004 may use the control message 2028, 2030 to decrease the threshold 2032 or keep the same threshold 2034, in certain examples. For example, if the physician indicates that the patient is not decompensating, then the verification module 2014 confirms that the physician's diagnosis is consistent with the result of the analysis 2008 and no change is made 2034 to the threshold value. However, if the physician determines that the patient is decompensating, then the verification module 2014 may communicate a verification message 2026 indicating that the analysis was incorrect and the threshold value may be decreased 2032 to increase the sensitivity of the analysis in later evaluations. By increasing the threshold value and making analysis more sensitive, the physician may affect the analysis to reduce false negatives in later evaluations. As with previously described case, the control message module 2020 may determine that decreasing the threshold is either impossible (e.g., due to a lower limit of an analytical technique or a sensor's particular capabilities) or impracticable, and in such a case, the control message module 2020 may generate a "No Change" message 2030.

Figure 21:
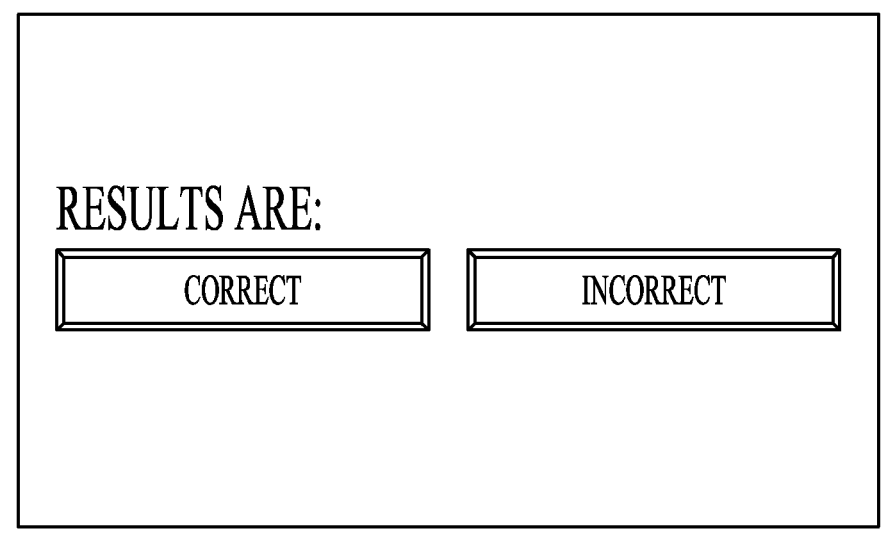

FIG. 21 is an example of a user-interface to allow a medical professional to submit input or feedback to a control system. In the example illustrated, a medical professional may provide an indication of whether a particular result of a diagnostic analysis is correct. In an example, a user is provided with the results of a particular analysis (e.g., heart failure decompensation risk) along with one or more patient physiological indications (e.g., heart rate intervals, implantable electrograms, electrogram templates for tachyarrhythmia detection or rhythm discrimination, pressure (e.g., intracardiac or systemic pressure), oxygen saturation, physical activity, heart rate variability, heart sounds, thoracic or intracardiac or other impedance, respiration, intrinsic depolarization amplitude, heart rate, data related to tachyarrhythmia episodes, hemodynamic stability, therapy history, autonomic balance, heart rate variability trends or templates, or trends, templates, or abstractions derived from sensed physiological data). The user may then evaluate the patient's condition and determine whether the results of the analysis are correct. Conceptually, in an example, the user takes the place of the verification module 2014 in FIG. 20.

Figure 22:
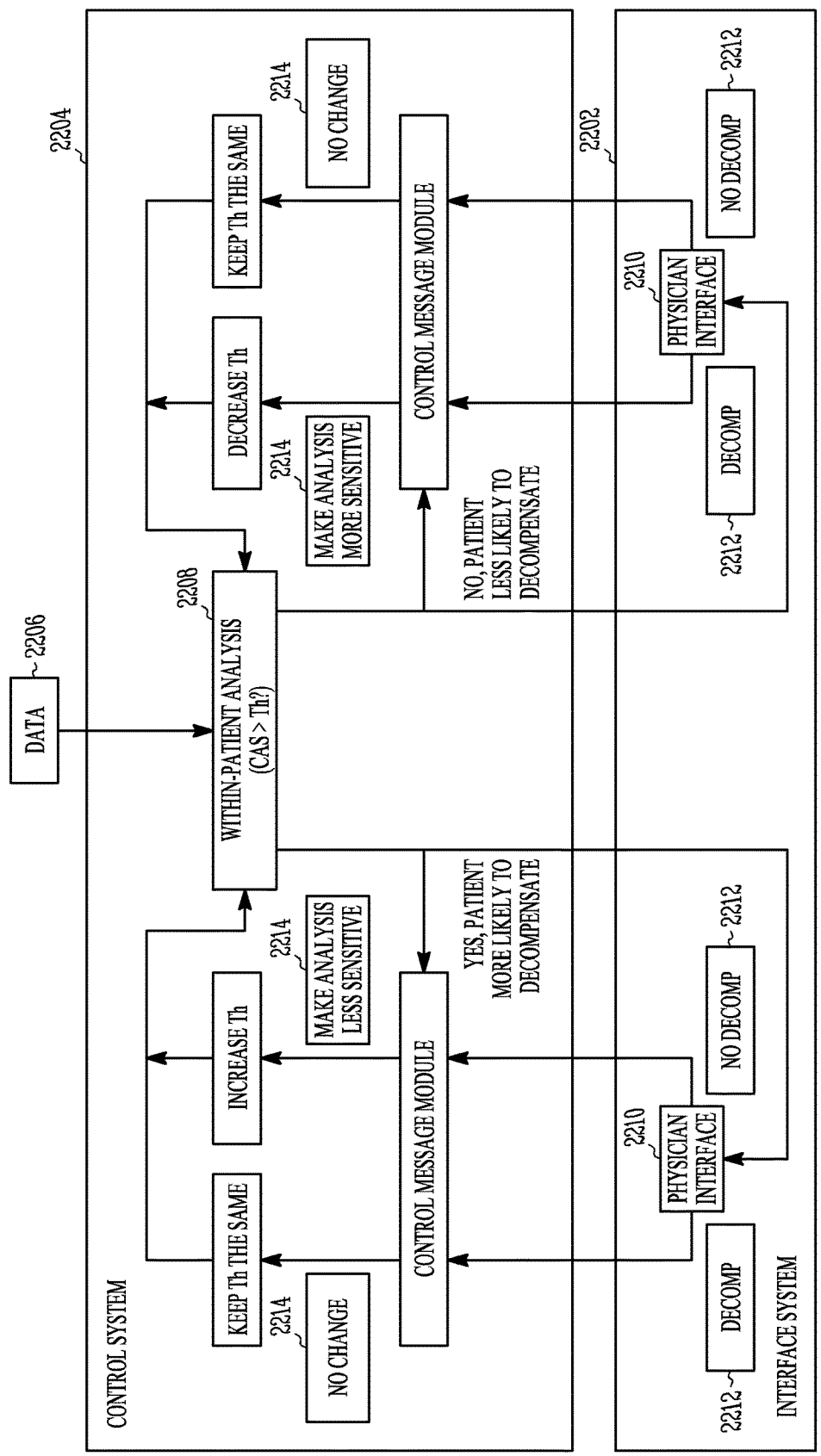
FIG. 22 is a control flow diagram illustrating an example of an interaction between a user-interface system and a control system in accordance with the user-interface illustrated in FIG. 21.

FIG. 22 is a control flow diagram illustrating an example of an interaction between a user-interface system 2202 and a control system 2204 in accordance with the user-interface illustrated in FIG. 21. In an example, the user-interface system 2202 is incorporated into a user terminal, such as illustrated in FIG. 1 at 112. In an example, the control system 2204 is incorporated into a remote server system, such as 108 in FIG. 1. In the example illustrated in FIG. 22, data 2206 is received by the control system 2204 and analyzed by a within-patient analysis 2208, such as within-patient analysis described herein. A composite alert score is evaluated and compared to a threshold value (Th). If the composite alert score is greater than the threshold (Th), then the status is presented to a physician interface 2210, such as for display. In examples, the physician interface 2210 may include a computer terminal, an electronic medical records system, or other input mechanism. A physician may use the provided information to confirm the results of the analysis. Unlike the situation illustrated in FIG. 20, the physician has foreknowledge of a result of the automated analysis, such that a patient evaluation is performed in response to the result and furthermore, to confirm the result. The physician may then provide the confirmation determination using the interface, such as an interface illustrated in FIG. 21. The physician's determination is communicated using a verification message 2212 in certain examples. In various examples, the verification message 2012 may be formatted using a standardized interface language, such as XML, or in a standard file format, such as comma-separated values (csv) or a tab delimited format. Similar to the operation illustrated in FIG. 20, the control system 2204 can use the verification message 2212 to generate one or more control messages 2214, which may direct the control system 2204 to modify the execution of the analysis 2208.

Figure 23:
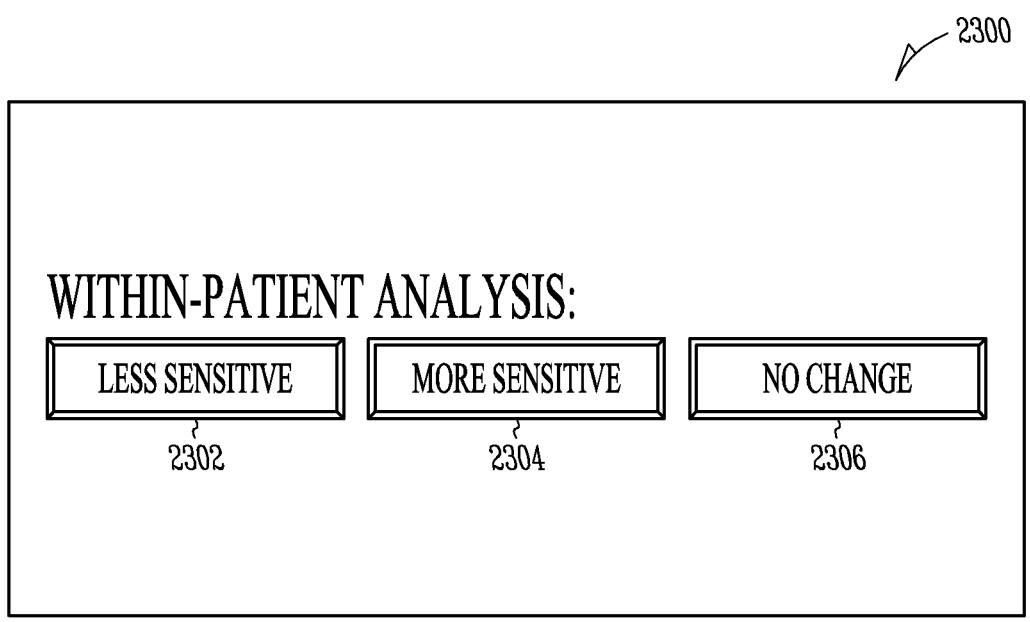
FIG. 23 is another example of a user-interface to allow a medical professional to submit feedback to a control system.

FIG. 23 is another example of a user-interface 2300 to allow a medical professional to submit feedback to a control system. In FIG. 23, the physician is provided controls 2302, 2304, 2306 to adjust the sensitivity of a patient analysis. When a physician activates one of the controls 2302, 2304, 2306, a control message is generated and communicated to the control system, in an example. The user-interface may be accessed, for example, during a patient evaluation where a physician has made an independent determination of the patient's status. If the physician concurs with the automatic patient analysis, then the physician may activate the "No Change" control 2306. If the physician believes that the patient analysis is incorrect and indicating a false positive, then the physician may decide to reduce the sensitivity of the analysis and activate the "Less Sensitive" control 2302. On the other hand, if the physician believes that the patient analysis is incorrect and indicating a false negative, then the physician may wish to increase the sensitivity of the analysis and active the "More Sensitive" control 2304. In other examples where multiple patient analysis techniques are used, a separate set of controls may be associated with each patient analysis technique and presented to the physician. In such a configuration, the physician may then have control over each analysis. In other examples, a single set of controls, such as those illustrated, are presented and may control multiple patient analysis techniques in an aggregate configuration. In addition, while controls that may be used to modify an algorithms sensitivity are illustrated in FIG. 23, in other examples, other controls may be provided to a user to control aspects of performance measures such as a false positive rate, a positive predictive value, a negative predictive value, or the like.

Figure 24:
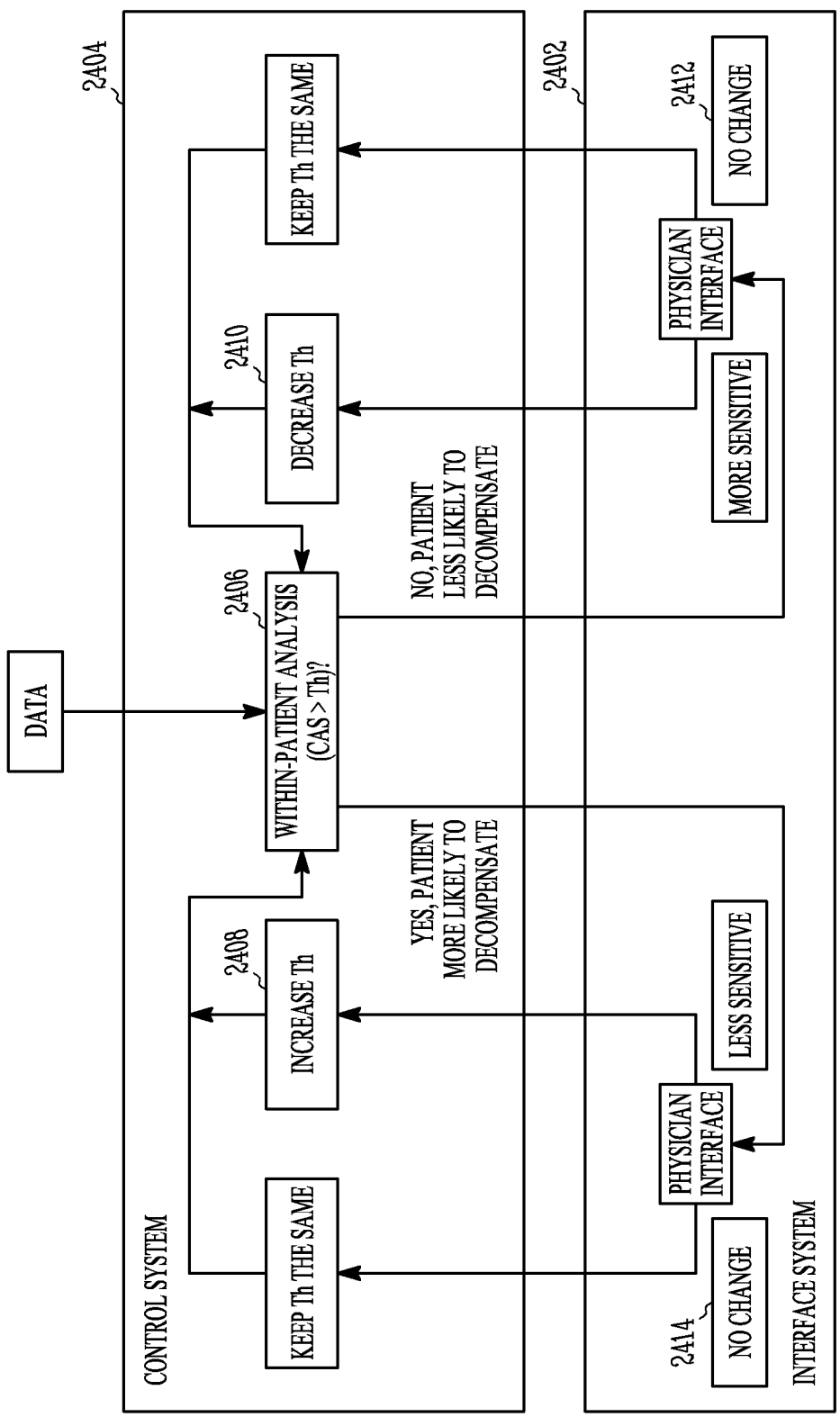
FIG. 24 is a control flow diagram illustrating an example of an interaction between a user-interface system and a control system in accordance with the user-interface illustrated in FIG. 23.

FIG. 24 is a control flow diagram illustrating an example of an interaction between a user-interface system 2402 and a control system 2404 in accordance with the user-interface illustrated in FIG. 23. Based on the result of the within-patient analysis 2406, the physician may determine that the result is incorrect and lower the sensitivity 2408 or raise the sensitivity 2410, depending on whether the incorrect result is perceived as a false positive of false negative, respectively. If the physician agrees with the within-patient analysis, then no change is indicated, such as in control messages 2412 and 2414. Control messages 2412, 2414 may be formatted using a standardized interface language, such as XML, or in a standard file format, such as comma-separated values (csv) or a tab delimited format.

Figure 25:
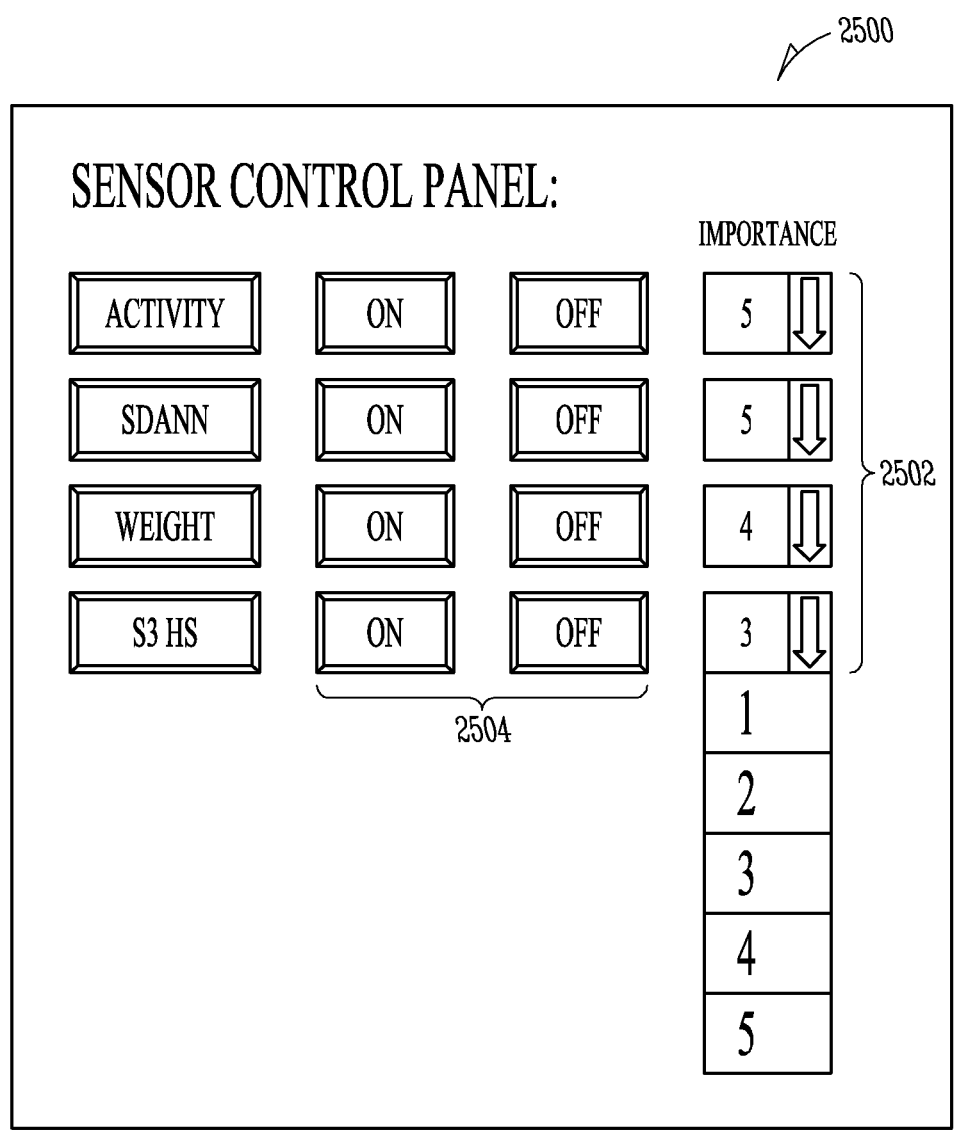
FIG. 25 is another example of a user-interface.

FIG. 25 is another example of a user-interface 2500. In FIG. 25, a user is provided one or more controls 2504 to activate or deactivate one or more sensors associated with a patient analysis technique. In the example illustrated, one or more sensors are associated with a heart failure decompensation evaluation. A user (e.g., a physician or clinician) may use the controls 2504 to manage whether each sensor result is used in the patient analysis (e.g., within-patient analysis). Controlling such aspects of the patient evaluation may be advantageous for physicians that wish to dismiss particularly unfavorable sensors or emphasize particularly favorable sensors for a particular patient. For example, a physician may have determined during their practice that a particular sensor is less determinative or less accurate when used in a particular patient's evaluation. Using controls illustrated in FIG. 25 would allow such a physician to remove such a sensor from the calculus of such a patient's status.

Additionally, the importance, or weight, of each sensor may be provided by the user by manipulating the importance controls 2502. The importance controls 2502 may be presented as a dropdown control containing the allowable range of values indicative of importance. In an example, each sensor may be associated with a default control, which may be indicated in the importance control 2502.

Figure 26:
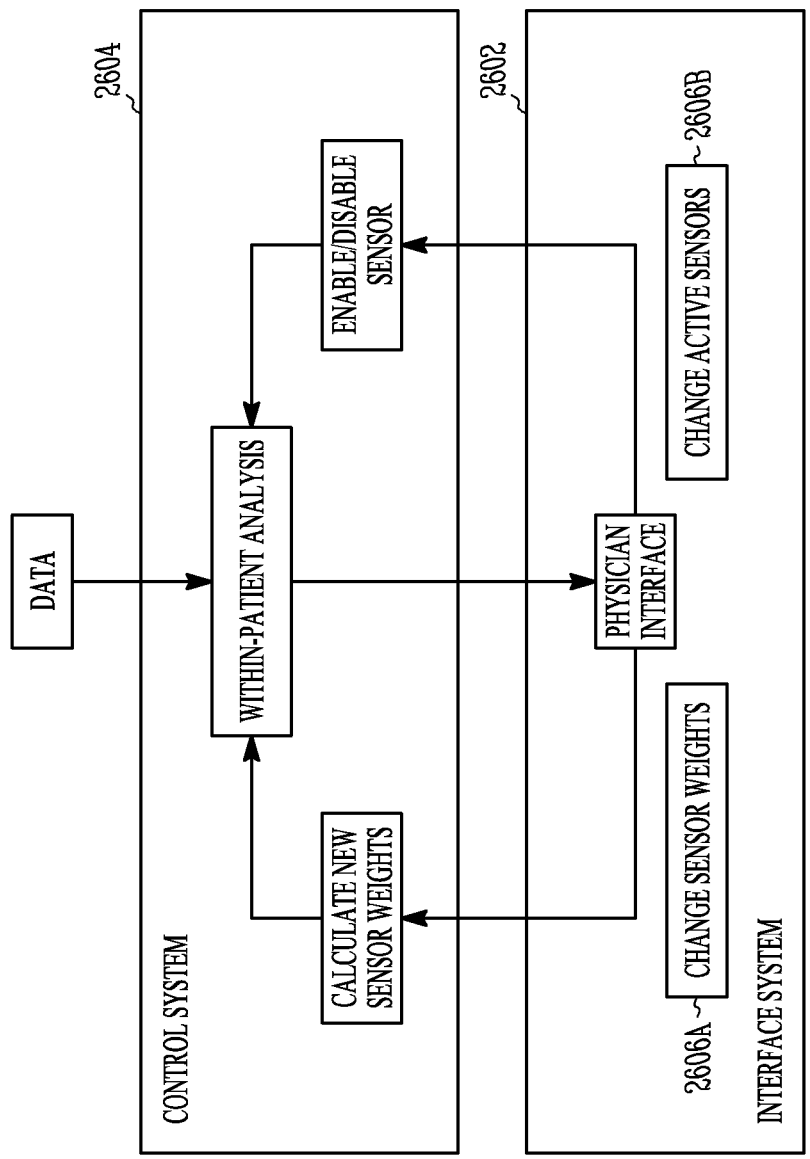
FIG. 26 is a control flow diagram illustrating an example of an interaction between a user-interface system and a control system in accordance with the user-interface illustrated in FIG. 25.

FIG. 26 is a control flow diagram illustrating an example of an interaction between a user-interface system 2602 and a control system 2604 in accordance with the user-interface illustrated in FIG. 25. The user may send one or more control messages 2606A, 2606B to change sensor weights or activate or deactivate particular sensors associated with a patient analysis.

Figure 27:
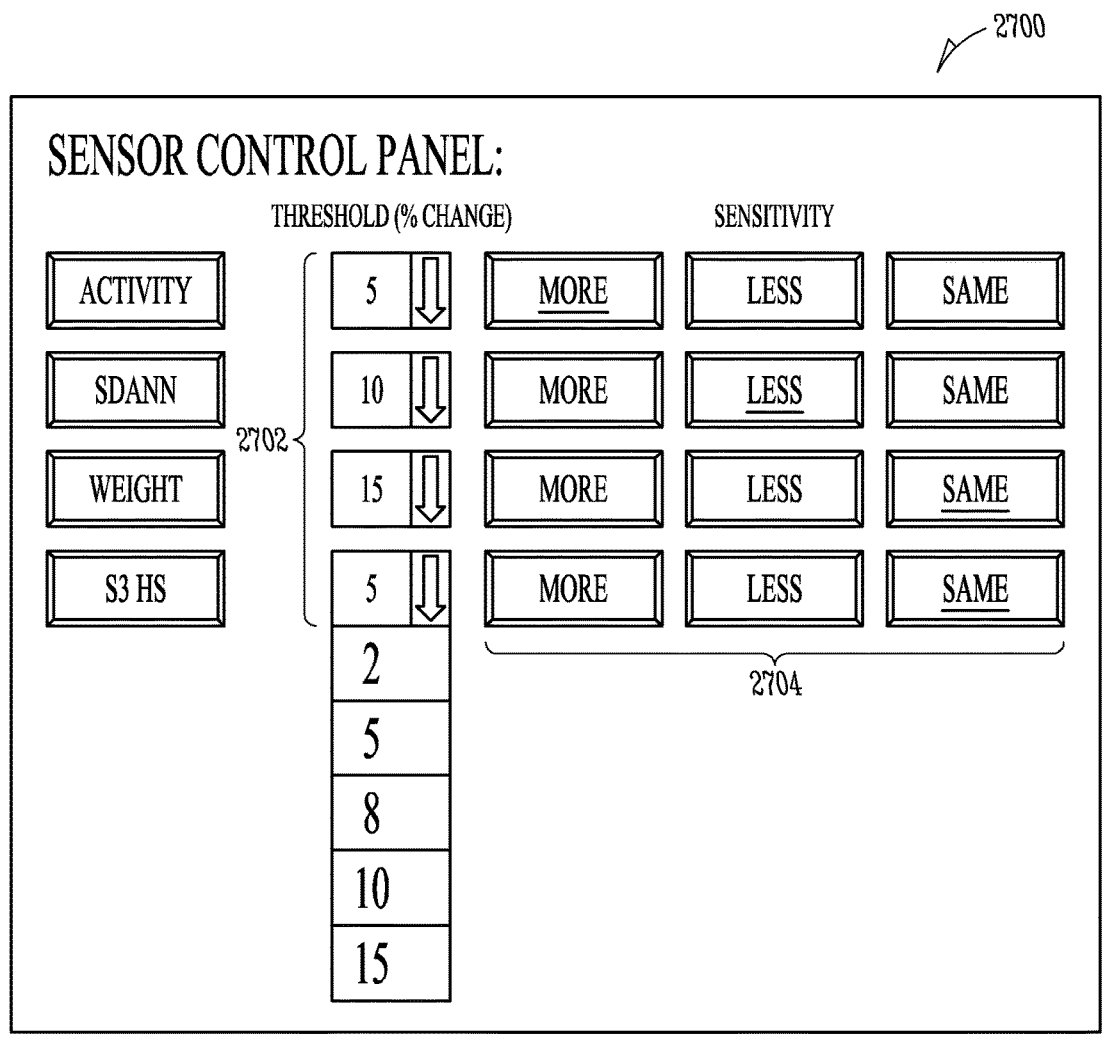
FIG. 27 is another example of a user-interface to control one or more sensors.

FIG. 27 is another example of a user-interface 2700 to control one or more sensors. For example, one or more controls may be provided to modify threshold values, modify sensitivity using general labels (e.g., "More Sensitive" or "Less Sensitive"), change the type of threshold computation used (e.g., an absolute value or a percent change from a baseline), or change a detection technique used by a particular sensor. In the example illustrated in FIG. 27, threshold controls 2702 are provided to a user to set threshold values, such as a function of a percent change from a particular value (e.g., a baseline value or an arbitrary initial value). In addition, sensitivity controls 2704 are provided so that a user may generally set a particular sensor to be more or less sensitive. The sensitivity controls 2704 may be configured to indicate a current setting to the user, such as using bold face, coloring, or other graphical or textual details that display to the user the current setting. In the example shown, when a user changes a threshold value to be higher than the current setting, thus decreasing the sensitivity, the general sensitivity control 2704 associated with the changed threshold control 2702 has its presentation altered to reflect the reduced sensitivity. Similarly, when a user selects a general sensitivity control 2704, a corresponding threshold value may be indicated in the associated threshold control 2702.

Figure 28:
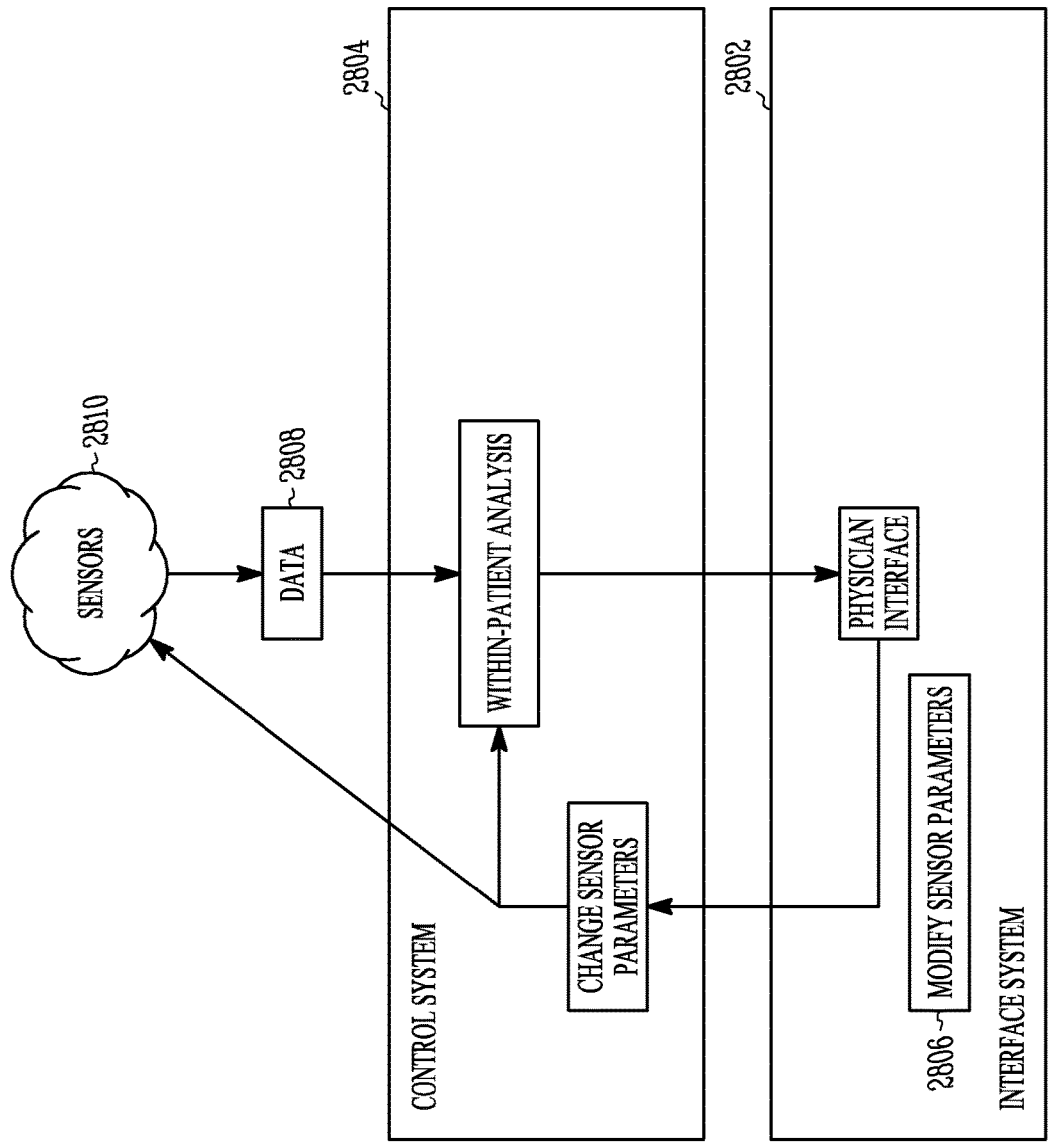
FIG. 28 is a control flow diagram illustrating an example of an interaction between a user-interface system and a control system in accordance with the user-interface illustrated in FIG. 27.

FIG. 28 is a control flow diagram illustrating an example of an interaction between a user-interface system 2802 and a control system 2804 in accordance with the user-interface illustrated in FIG. 27. The user of the user-interface system 2802 may send one or more control messages 2806 to the control system 2804 to change one or more threshold values associated with one or more sensors, change the sensitivity of one or more sensors, manage the detection techniques used on one or more sensors, or perform other management tasks as described with regard to the user-interface in FIG. 27. In an example, the control system 2804 may receive unmodified, sensed data 2808 from one or more sensors 2810. The control system 2804 may then analyze the data 2808 and set one or more alerts using the modified threshold values, sensitivity levels, or other user-provided inputs, and ultimately derive the composite alert score. In other words, the control system 2804 may retain the user-provided information and manage the alerts local to the control system 2804. In another example, the control system 2804 may communicate the threshold values, sensitivity levels, or other user-provided information to one or more sensors 2810 corresponding to the sensors presented in a user-interface, such as in FIG. 27. In such an example, each sensor 2810 may then modify its own internal detection algorithm and provide appropriate alerts using the new threshold values, for example.

Some of all of the user-interfaces described in FIGS. 19, 21, 23, 25, 27 may be combined in various combinations or permutations to grant differing scopes of control to a user. Additionally, other user-interfaces not illustrated may be provided to a user to control other aspects of patient analysis techniques, such as analysis blending, sensor blending, timing intervals of sensor fusion over time, sensor settings, detection thresholds, selected population groups, or the like.

As described above, centralized data may be advantageous for several reasons. For example, physicians may be able to share data easier in the situation where patients see several health care providers who are not members of the same medical practice and thus, does not have access to each other's EMR database. In addition, centralized data may provide greater insight into patient health trends when using systems and methods as described herein.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. For example, although the description describes a particular example in which information is provided to a medical practice, in other examples, one or more other users obtain such information using the present systems and methods. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

For the purposes of this specification, the term "machine-readable medium" or "computer-readable medium" shall be taken to include any medium which is capable of storing or encoding a sequence of instructions for execution by the machine and that cause the machine to perform any one of the methodologies of the inventive subject matter. The terms "machine-readable medium" or "computer-readable medium" shall accordingly be taken to include, but not be limited to, solid-state memories, optical and magnetic disks, and other temporary, transient, or permanent storage means, such an executable streaming downloadable program. Further, it will be appreciated that the software could be distributed across multiple machines or storage media, which may include the machine-readable medium.

Method embodiments described herein may be computer-implemented. Some embodiments may include computer-readable media encoded with a computer program (e.g., software), which includes instructions operable to cause an electronic device to perform methods of various embodiments. A software implementation (or computer-implemented method) may include microcode, assembly language code, or a higher-level language code, which further may include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The Abstract is provided to comply with 37 C.F.R. § 1.72(b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A method comprising:
receiving, by a transceiver, patient data at a processor-based system from a sensor, the patient data comprising patient physiological data;
using the patient data at the processor-based system in an automated diagnostic technique to obtain a result reflecting a first physiological event, wherein the diagnostic technique is a programmatic code;
communicating the result to a clinician through a user interface;
receiving, by the processor-based system, a message from the clinician, wherein the message includes a clinician observation of the patient;
comparing, by a verification module, the clinician observation to the result to determine that the clinician observation is inconsistent with the result;
modifying, by the processor-based system, the diagnostic technique for a subsequent performance of the diagnostic technique based on comparing the clinician observation to the result, wherein the processor-based system uses the clinician observation to modify the diagnostic technique, and
executing the modified diagnostic technique to obtain a new result.

2. The method of claim 1, wherein the message includes one or more parameters to improve the performance of the diagnostic technique.

3. The method of claim 2, wherein the parameters include one or more of: a threshold, an indication of a specificity, or an indication of a sensitivity.

4. The method of claim 1, wherein the clinician observation of the patient includes a result of an independent assessment of the patient, wherein the independent patient assessment is used to determine a result that is comparable to the result of the diagnostic technique.

5. The method of claim 1, wherein using the patient data includes determining a patient condition.

6. The method of claim 1, wherein the message is formatted using a standardized interface language.

7. The method of claim 6, wherein the standardized interface language includes XML.

8. The method of claim 1, wherein using the result and the clinician observation to automatically modify the diagnostic technique includes adjusting a sensitivity of the diagnostic technique based on the indication of the accuracy of the result.

9. The method of claim 8, wherein adjusting a sensitivity of the diagnostic technique includes adjusting a threshold used in the diagnostic technique.

10. The method of claim 1, wherein using the result and the clinician observation to automatically modify the diagnostic technique includes adjusting a specificity of the diagnostic technique based on the indication of the accuracy of the result.

11. The method of claim 10, wherein adjusting a specificity of the diagnostic technique includes adjusting a threshold used in the diagnostic technique.

12. The method of claim 1, wherein using the result and the clinician observation comprises:
comparing the result to the clinician observation to obtain a comparison; and
based on the comparison, modifying the diagnostic technique in subsequent performance of the diagnostic technique.

13. A system comprising:
a transceiver adapted to receive patient data from a sensor, the patient data comprising patient physiological data;
a storage device having a programmatic code defining an automated diagnostic technique;
an operating device comprising an analysis module adapted to execute the automated diagnostic technique and to use the patient data in the automated diagnostic technique to obtain a result reflecting risk of a first physiological event;
a user-interface configured to:
communicate the result to a clinician; and
receive a message from the clinician, wherein the message includes a clinician observation of the patient; and
a verification module configured to determine whether the observation is inconsistent with the result, wherein the analysis module is further adapted to use the clinician observation to modify the diagnostic technique for subsequent performance of the diagnostic technique if the message is inconsistent with the result, and wherein the analysis module is further adapted to maintain the diagnostic technique if the message is consistent with the result.

14. The system of claim 13, wherein the message includes one or more parameters to improve the performance of the diagnostic technique.

15. The system of claim 14, wherein the parameters include one or more of: a threshold, an indication of a specificity, or an indication of a sensitivity.

16. The system of claim 13, wherein the clinician observation of the patient includes a result of an independent assessment of the patient, wherein the independent patient assessment is used to determine a result that is comparable to the result of the diagnostic technique.

17. The system of claim 13, wherein a communication module is included at a central system.

18. The system of claim 13, wherein the analysis module is further adapted to use the patient data to determine a patient condition.

19. The system of claim 13, wherein the analysis module is adapted to adjust at least one of a sensitivity or a specificity of the diagnostic technique based on the result and the clinician observation.

20. The system of claim 13, wherein the analysis module is adapted to:
compare the result to the clinician observation to obtain a comparison; and
based on the comparison, modify the diagnostic technique in subsequent performance of the diagnostic technique.

21. An apparatus comprising:
means for receiving patient data from a sensor, the patient data comprising patient physiological data;
means for using the patient data in an automated diagnostic technique to obtain a result reflecting risk of a first physiological event, wherein the diagnostic technique is a programmatic code;

means for communicating the result to a clinician;
means for receiving a message from the clinician, wherein the message includes a clinician observation of the patient;
means for determining whether the observation is inconsistent with the result;
means for selectively modifying the diagnostic technique using the clinician observation for a subsequent performance of the diagnostic technique if the message is inconsistent with the result, and for executing the modified diagnostic technique to obtain a new result; and
a means for maintaining the current diagnostic technique if the message is consistent with the result.

* * * * *